United States Patent
McKittrick et al.

(10) Patent No.: US 8,110,682 B2
(45) Date of Patent: Feb. 7, 2012

(54) PREPARATION AND USE OF COMPOUNDS AS ASPARTYL PROTEASE INHIBITORS

(75) Inventors: Brian McKittrick, New Vernon, NJ (US); Zhaoning Zhu, Plainsboro, NJ (US); Andrew Stamford, Chatham Township, NJ (US); Elizabeth M. Smith, Verona, NJ (US)

(73) Assignee: Schering Corporation, Kenilworth, NJ (US)

( * ) Notice: Subject to any disclaimer, the term of this patent is extended or adjusted under 35 U.S.C. 154(b) by 1254 days.

(21) Appl. No.: 11/451,262

(22) Filed: Jun. 12, 2006

(65) Prior Publication Data

US 2007/0010667 A1   Jan. 11, 2007

Related U.S. Application Data

(60) Provisional application No. 60/690,413, filed on Jun. 14, 2005.

(51) Int. Cl.
| | |
|---|---|
| C07D 251/42 | (2006.01) |
| C07D 251/16 | (2006.01) |
| C07D 251/22 | (2006.01) |
| A61K 31/53 | (2006.01) |
| A61P 3/10 | (2006.01) |

(52) U.S. Cl. ........ 544/180; 544/220; 514/241; 514/245; 514/246

(58) Field of Classification Search .......... 544/180, 544/220; 514/241, 245, 246
See application file for complete search history.

(56) References Cited

U.S. PATENT DOCUMENTS

| | | | | |
|---|---|---|---|---|
| 3,287,365 | A * | 11/1966 | Newman et al. | 544/206 |
| 3,287,366 | A * | 11/1966 | Newman et al. | 544/206 |
| 3,632,762 | A * | 1/1972 | Mamalis et al. | 514/245 |
| 3,682,912 | A * | 8/1972 | Mamalis et al. | 544/206 |
| 3,723,429 | A * | 3/1973 | Mamalis et al. | 544/206 |
| 3,876,785 | A * | 4/1975 | Mamalis | 514/245 |
| 5,565,451 | A * | 10/1996 | Peake et al. | 514/245 |
| 6,232,309 | B1 * | 5/2001 | Shiokawa et al. | 514/222.5 |
| 6,645,915 | B1 * | 11/2003 | Riebel et al. | 504/234 |
| 7,256,218 | B2 * | 8/2007 | Jacobus et al. | 514/633 |
| 7,642,247 | B2 * | 1/2010 | Daifuku et al. | 514/43 |
| 2003/0109530 | A1 * | 6/2003 | Moinet et al. | 514/245 |
| 2003/0203908 | A1 * | 10/2003 | Lowe | 514/245 |
| 2005/0282825 | A1 | 12/2005 | Malamas et al. | |
| 2005/0282826 | A1 | 12/2005 | Malamas et al. | |
| 2006/0154928 | A1 * | 7/2006 | Maeda et al. | 514/241 |
| 2008/0200445 | A1 * | 8/2008 | Zhu et al. | 514/210.02 |

FOREIGN PATENT DOCUMENTS

| | | | |
|---|---|---|---|
| FR | 1298322 | A * | 6/1962 |
| SE | 78331 | A * | 7/1964 |
| WO | WO 93/04047 | | 3/1993 |
| WO | WO 02/074719 | A2 | 9/2002 |
| WO | WO 2006/041404 | A1 | 4/2006 |
| WO | WO2006/044497 | A2 | 4/2006 |
| WO | WO 2006/065277 | A2 | 6/2006 |

OTHER PUBLICATIONS

Eder et al. Current Pharmacological Design, 13, 271-285, 2007.*
West, Anthony R., Solid State Chemistry and its Applications, Wiley, New York, 1988, pp. 358 & 365.*
Vippagunta et al., Advanced Drug Delivery Reviews 48: 3-26, 2001.*
Sheers,E., Journal of Organic Chemistry, 25, 147-148, 1960.*
Piskala, Collection of Czechoslovak Chemical Communications (1967), 32(12), 4271-9; CA 68:29978, 1968.*
Zhu et al., US20080200445; CA 149; 307842, 2008.*
Turner et al. J. Med. Chem., 28, 1728-1740, 1985.*
Modest et al. J. Org. Chem., 21(1), 14-20, 1956.*
Rosowsky et al. Antimicrobial Agents and Chemotherapy 39(1), 79-86, 1995.*
Baker B.R., Journal of Medicinal Chemistry, 10(5), 912-917, 1967.*
Genther, Journal of Medicinal Chemistry, 20(2), 237-243, 1977.*
Coats, Journal of Medicinal Chemistry, 28(12), 1910-1916, 1985.*
Chio et al. Antimicrobial Agents and Chemotherapy 37(5), 1914-1923, 1993.*
Roger et al. Eur. J. Med. Chimica Therapeutica12(6), 495-500, 1977.*

(Continued)

*Primary Examiner* — Venkataraman Balasubramanian
(74) *Attorney, Agent, or Firm* — Keith D. MacMillan; Gerard M. Devlin

(57) ABSTRACT

Disclosed are compounds of the formula I

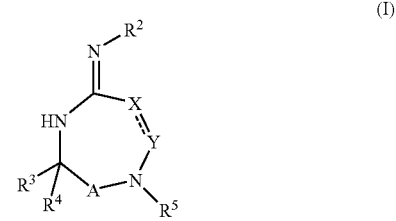

(I)

or a stereoisomer, tautomer, or pharmaceutically acceptable salt or solvate thereof,
wherein
A is a bond, —C(O)—, or —C(R$^{3'}$)(R$^{4'}$)—;
X is —N(R$^1$)— or —C(R$^6$)(R$^7$)—;
Y is —S(O)$_2$—, —C(=O)—, —PO(OR$^9$) or —C(R$^6$R$^7$)—;
------ is a single or double bond
and R, R$^1$, R$^2$, R$^3$, R$^4$, R$^{3'}$, R$^{4'}$, R$^5$, R$^6$, R$^{6'}$, R$^7$ and R$^{7'}$ are as defined in the specification; and pharmaceutical compositions comprising the compounds of formula I.
Also disclosed is the method of inhibiting aspartyl protease, and in particular, the methods of treating cardiovascular diseases, cognitive and neurodegenerative diseases, and the methods of inhibiting of Human Immunodeficiency Virus, plasmepins, cathepsin D and protozoal enzymes.
Also disclosed are methods of treating cognitive or neurodegenerative diseases using the compounds of formula I in combination with a cholinesterase inhibitor or a muscarinic antagonist.

15 Claims, No Drawings

OTHER PUBLICATIONS

Bartlett et al. Antimicrobial Agents and Chemotherapy 39(11), 2436-2441, 1995.*

Na et al., Aspartic proteases of plasmodium vivax are highly conserved in wild isolates, Korean Journal of Prasiology (Jun. 2004), 42(2) 61-6, Journal Code: 9435800.

Moore et al., Purification of HTLS-I Protease and Synthesis of Inhibitors for the treatment of HTLV-I Invention. 55th South East Regional Meeting of the American Chemical Society, Atlanta, GA, (Nov. 2003) 1073 CODEN; 69EUCH Conference. AN 2004: 137641 CAPLUS (Abstract 5 Pages).

Oparil et al., The Renin-Angioensin System (Second of Two Parts), The New England Journal of Medicine, (Aug. 1974), 291(9) 446-457.

U.S. Appl. No. 11/010,772 filed on Dec. 13, 2004-325 Pages.

Chemical Abstract Service, Columbus, Ohio, US; XP002407972, Database accession No. 1929-36029, Ostrogovish, Adriano et al., "Some New aryliminoxy-.gamma.-triazidinic derivatiers. I" Gazzetta Chimica Italiana, 59, 181-98 CODEN: GCITA9; ISSN: 0016-5603. 1929.

Database Beilstein, XP0020407973, Database accession No. 6091897, Vovk, M. V., I.F. Chem. Heterocycl. Compd. (Engl. Transl), vol. 33, No. 5. 1997, p. 614-618.

Wendell W. Wilkerson et al., XP002407903, "HIV Protease Inhibitory Bis-benzamide Cyclic Ureas: A Quantitative Structure-Activity Relationship Analysis", J. Med. Chem., vol. 39, No. 21, 1996, p 4299-4312.

International Search Report PCT/US2006/022920.

* cited by examiner

PREPARATION AND USE OF COMPOUNDS AS ASPARTYL PROTEASE INHIBITORS

RELATED APPLICATIONS

This application claims priority to provisional application U.S. Ser. No. 60/690,413, filed on Jun. 14, 2005, herein incorporated by reference.

FIELD OF THE INVENTION

This invention relates to heterocyclic compounds, which function as aspartyl protease inhibitors, their preparation, pharmaceutical compositions comprising said compounds, their use in the treatment of cardiovascular diseases, cognitive and neurodegenerative diseases, and their use as inhibitors of the Human Immunodeficiency Virus, plasmepsins, cathepsin D and protozoal enzymes.

BACKGROUND

There are a number of aspartic proteases known to date, including pepsin A and C, renin, BACE, BACE 2, Napsin A, and cathepsin D, which have been implicated in pathological conditions.

The role of renin-angiotensin system (RAS) in regulation of blood pressure and fluid electrolyte has been well established (Oparil, S, et al. N Engl J Med 1974; 291:381-401/446-57). The octapeptide Angiotensin-II, a potent vasoconstrictor and stimulator for release of adrenal aldosterone, was processed from the precursor decapeptide Angiotensin-I, which in turn was processed from angiotensinogen by the renin enzyme. Angiotensin-II was also found to play roles in vascular smooth muscle cell growth, inflammation, reactive oxygen species generation and thrombosis, influence atherogenesis and vascular damage. Clinically, the benefit of interruption of the generation of angiotensin-II through antagonism of conversion of angiotensin-I has been well known and there are a number of ACE inhibitor drugs on the market. The blockade of the earlier conversion of angiotensinogen to angiotensin-I, i.e. the inhibition of renin enzyme, is expected to have similar but not identical effects. Since renin is an aspartyl protease whose only natural substrate is angiotensinogen, it is believed that there would be less frequent adverse effect for controlling high blood pressure and related symptoms regulated by angiotensin-II through its inhibition.

Another protease, Cathespin-D, is involved in lysosomal biogenesis and protein targeting, and may also be involved in antigen processing and presentation of peptide fragments. It has been linked to numerous diseases including, Alzheimer's, disease, connective tissue disease, muscular dystrophy and breast cancer.

Alzheimer's disease (AD) is a progressive neurodegenerative disease that is ultimately fatal. Disease progression is associated with gradual loss of cognitive function related to memory, reasoning, orientation and judgment. Behavioral changes including confusion, depression and aggression also manifest as the disease progresses. The cognitive and behavioral dysfunction is believed to result from altered neuronal function and neuronal loss in the hippocampus and cerebral cortex. The currently available AD treatments are palliative, and while they ameliorate the cognitive and behavioral disorders, they do not prevent disease progression. Therefore there is an unmet medical need for AD treatments that halt disease progression.

Pathological hallmarks of AD are the deposition of extracellular β-amyloid (Aβ) plaques and intracellular neurofibrillary tangles comprised of abnormally phosphorylated protein tau. Individuals with AD exhibit characteristic Aβ deposits, in brain regions known to be important for memory and cognition. It is believed that Aβ is the fundamental causative agent of neuronal cell loss and dysfunction which is associated with cognitive and behavioral decline. Amyloid plaques consist predominantly of Aβ peptides comprised of 40-42 amino acid residues, which are derived from processing of amyloid precursor protein (APP). APP is processed by multiple distinct protease activities. Aβ peptides result from the cleavage of APP by β-secretase at the position corresponding to the N-terminus of Aβ, and at the C-terminus by γ-secretase activity. APP is also cleaved by α-secretase activity resulting in the secreted, non-amyloidogenic fragment known as soluble APP.

An aspartyl protease known as BACE-1 has been identified as the β-secretase activity responsible for cleavage of APP at the position corresponding to the N-terminus of Aβ peptides.

Accumulated biochemical and genetic evidence supports a central role of Aβ in the etiology of AD. For example, Aβ has been shown to be toxic to neuronal cells in vitro and when injected into rodent brains. Furthermore inherited forms of early-onset AD are known in which well-defined mutations of APP or the presenilins are present. These mutations enhance the production of Aβ and are considered causative of AD.

Since Aβ peptides are formed as a result β-secretase activity, inhibition of BACE-1 should inhibit formation of Aβ peptides. Thus inhibition of BACE-1 is a therapeutic approach to the treatment of AD and other cognitive and neurodegenerative diseases caused by Aβ plaque deposition.

Human immunodeficiency virus (HIV), is the causative agent of acquired immune deficiency syndrome (AIDS). Traditionally, a major target for researchers has been HIV-1 protease, an aspartyl protease related to renin. It has been clinically demonstrated that compounds such as indinavir, ritonavir and saquinavir which are inhibitors of the HIV aspartyl protease result in lowering of viral load. As such, the compounds described herein would be expected to be useful for the treatment of AIDS.

In addition, Human T-cell leukemia virus type I (HTLV-I) is a human retrovirus that has been clinically associated with adult T-cell leukemia and other chronic diseases. Like other retroviruses, HTLV-I requires an aspartyl protease to process viral precursor proteins, which produce mature virions. This makes the protease an attractive target for inhibitor design. (Moore, et al. Purification of HTLV-I Protease and Synthesis of Inhibitors for the treatment of HTLV-I Infection 55th Southeast Regional Meeting of the American Chemical Society, Atlanta, Ga., US Nov. 16-19, 2003 (2003), 1073. CODEN; 69EUCH Conference, AN 2004:137641 CAPLUS.)

Plasmepsins are essential aspartyl protease enzymes of the malarial parasite. Compounds for the inhibition of aspartyl proteases plasmepsins, particularly I, II, IV and HAP, are in development for the treatment of malaria. (Freire, et al. WO 2002074719. Na Byoung-Kuk, et al. Aspartic proteases of *Plasmodium vivax* are highly conserved in wild isolates Korean Journal of Prasitology (2004 June), 42(2) 61-6. Journal code: 9435800.) Furthermore, compounds used to target aspartyl proteases plasmepsins (e.g. I, II, IV and HAP), have been used to kill malarial parasites, thus treating patients thus afflicted. Certain compounds also exhibited inhibitory activity against Cathespin D.

Compounds that act as aspartyl protease inhibitors are described, for example, in application U.S. Ser. No. 11/010, 772, filed on Dec. 13, 2004, herein incorporated by reference.

WO/9304047, herein incorporated by reference, describes compounds having a quinazolin-2-(thi)one nucleus. The document alleges that the compounds described therein are inhibitors of HIV reverse transcriptase.

US Publication No. US 2005/0282826 A1, herein incorporated by reference, describes diphenylimidazopyrimidine or -imidazole amines, which are said to be useful for the therapeutic treatment, prevention or amelioration of a disease or disorder characterized by elevated β-amyloid deposits or β-amyloid levels in a patient. Disease states mentioned in the publication include Alzheimer's disease, mild cognitive impairment, Down's syndrome, hereditary cerebral hemorrhage with amyloidosis of the Dutch type, cerebral amyloid angiopathy and degenerative dementia.

US Publication No. US 2005/0282825 A1, herein incorporated by reference, describes amino-5,5-diphenylimidazolones, which are said to be useful for the therapeutic treatment, prevention or amelioration of a disease or disorder characterized by elevated β-amyloid deposits or β-amyloid levels in a patient. Disease states mentioned in the publication include Alzheimer's disease, mild cognitive impairment, Down's syndrome, hereditary cerebral hemorrhage with amyloidosis of the Dutch type, cerebral amyloid angiopathy and degenerative dementia.

Other publications that disclosed compounds that are useful for treating Alzherimer's disease include WO 2006/044492, which discloses spiropiperidine compounds that are said to be inhibitors of β-secretase, and WO 2006/041404, which discloses substituted amino compounds that are said to be useful for the treatment or prophylaxis of Aβ related pathologies. Both these publications are incorporated by reference.

SUMMARY OF THE INVENTION

The present invention relates to compounds having the structural formula I

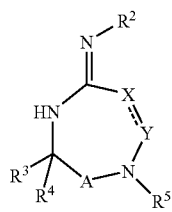

(I)

or a stereoisomer, tautomer, or pharmaceutically acceptable salt or solvate thereof, wherein A is a bond, —C(O)—, or —C(R$^{3'}$)(R$^{4'}$)—;
X is —N(R$^1$)— or —C(R$^6$)(R$^7$)—;
Y is —S(O)$_2$—, —C(=O)—, —PO(OR$^9$) or —C(R$^{6'}$R$^{7'}$)—;
----- is a single or double bond;
and optionally,
(i) R$^4$ and R$^5$ together form a 4- to 7-membered heterocyclyl, heterocyclenyl or heteroaryl ring having, in addition to the N atom, 1 or 2 additional hetero atoms selected from the group consisting of O, N, —N(R)— and S, wherein said rings are optionally substituted by 1 to 5 independently selected R$^{14}$ moieties and/or by oxo when said rings are heterocyclyl or heterocyclenyl;
(ii) when Y is —C(R$^{6'}$R$^{7'}$), R$^5$ and R$^{6'}$ together form a 4- to 7-membered heterocyclyl, heterocyclenyl or heteroaryl ring having in addition to the N atom 1 or 2 additional heteroatoms selected from the group consisting of O, N, —N(R)—, and S, wherein said rings are or 1 to 5 independently selected R$^{14}$ moieties and/or by oxo when said rings are heterocyclyl or heterocyclenyl;
(iii) when a) X is N(R$^1$) and Y is —C(R$^{6'}$)(R$^{7'}$)—, R$^1$ and R$^{6'}$ together form a 4- to 7-membered heterocyclyl, heterocyclenyl or heteroaryl ring having in addition to the N atom 1 or 2 additional heteroatoms selected from the group consisting of O, N, —N(R)—, and S, wherein said rings are optionally substituted by 1 to 5 independently selected R$^{14}$ moieties or by oxo when said rings are heterocyclyl or heterocyclenyl; or b) X is —C(R$^6$)(R$^7$)— and Y is —C(R$^{6'}$)(R$^{7'}$)—, R$^6$ and R$^{6'}$ together form a 5- to 7-membered cycloalkyl, cycloalkenyl, heterocyclyl, heterocyclenyl, aryl or heteroaryl ring having 0 to 3 heteroatoms selected from the group consisting of O, N, —N(R)— and S, wherein said rings are optionally substituted by 1 to 5 independently selected R$^{14}$ moieties and/or by oxo when said rings are cycloalkyl, cycloalkenyl, heterocyclyl or heterocyclenyl;
(iv) when R$^4$ and R$^5$ together form a 4- to 7-membered heterocyclyl, heterocyclenyl or heteroaryl ring, as defined above, and either: a) X is N(R$^1$) and Y is —C(R$^{6'}$)(R$^{7'}$)— or b) X is —C(R$^6$)(R$^7$)— and Y is C(R$^{6'}$)(R$^{7'}$)—, then either a) R$^1$ and R$^{6'}$ or b) R$^6$ and R$^{6'}$ together form a 3- to 7-membered cycloalkyl, cycloalkenyl, heterocyclyl, heterocyclenyl, aryl or heteroaryl ring having 0 to 3 heteroatoms selected from the group consisting of O, N, —N(R)— and S, wherein said rings are optionally substituted by 1 to 5 independently selected R$^{14}$ moieties and/or oxo when said rings are cycloalkyl, cycloalkenyl, heterocyclyl or heterocyclenyl; or
(v) when A is —C(R$^{3'}$)(R$^{4'}$), either:
 i) R$^{4'}$ and R$^4$ together form a 3- to 7-membered cycloalkyl, cycloalkenyl, heterocyclyl, heterocyclenyl, aryl or heteroaryl ring having 0 to 3 heteroatoms selected from the group consisting of O, N, —N(R)— and S, wherein said rings are optionally substituted by 1 to 5 independently selected R$^{14}$ moieties or oxo when said rings are cycloalkyl, cycloalkenyl, heterocyclyl or heterocyclenyl; or
 ii) R$^{4'}$ and R$^5$ together form a 4- to 7-membered heterocyclyl, heterocyclenyl or heteroaryl ring having, in addition to the N atom, 1 or 2 additional hetero atoms selected from the group consisting of O, N, —N(R)— and S, wherein said rings are optionally substituted by 1 to 5 independently selected R$^{14}$ moieties and/or by oxo when said rings are heterocyclyl or heterocyclenyl provided that i) R$^4$ and R$^5$ and ii) R$^5$ and R$^{6'}$ cannot cyclize to form a ring at the same time;

R is hydrogen, alkyl, alkenyl, alkynyl, cycloalkyl, cycloalkenyl, aryl, arylalkyl, heterocycloalkyl, heterocycloalkylalkyl, heteroaryl, heteroarylalkyl, arylcycloalkyl, —OR$^{15}$, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), or —S(O)$_2$N(R$^{11}$)(R$^{12}$);

R$^1$, R$^2$ and R$^5$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, —OR$^{15}$, —CN, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), —S(O)$_2$N(R$^{11}$)(R$^{12}$), —NO$_2$, —N=C(R$^8$)$_2$ and —N(R$^8$)$_2$;

R$^3$ and R$^4$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, cycloalkenylheteroaryl, heterocycloalkenylheteroaryl, —CH$_2$—O—Si(R$^9$)(R$^{10}$)(R$^{19}$), —CN, —C(O)R$^8$, —C(O)OR$^9$, —C(O)N(R$^{11}$)(R$^{12}$), —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S(O)R$^{10}$, —N(R$^{11}$)S(O)$_2$R$^{10}$—, —N(R$^{11}$)C(O)N(R$^{12}$)(R$^{13}$), —N(R$^{11}$)C(O)OR$^9$ and —C(=NOH)R$^8$;

or optionally, R$^3$ and R$^4$ together with the carbon atom to which they are attached form: a) a 3- to 7-membered cycloalkyl ring optionally substituted by 1 to 5 R$^{14}$ moieties or oxo; or b) a 3- to 7-membered cycloalkylether group having one oxygen atom optionally substituted by 1 to 5 R$^{14}$ moieties and/or oxo;

R$^{3'}$ and R$^{4'}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, —CH$_2$—O—Si(R$^9$)(R$^{10}$)(R$^{19}$), —CN, —C(O)R$^8$, —C(O)OR$^9$, —C(O)N(R$^{11}$)(R$^{12}$), —S(O)N(R$^{11}$)(R$^{12}$), —S(O)$_2$N(R$^{11}$)(R$^{12}$), —N(R$^{11}$)C(O)R$^8$, —N(R$^{11}$)S(O)R$^{10}$, —N(R$^{11}$)S(O)$_2$R$^{10}$—, —N(R$^{11}$)C(O)N(R$^{12}$)(R$^{13}$), —N(R$^{11}$)C(O)OR$^9$ and —C(=NOH)R$^8$;

or optionally, R$^{3'}$ and R$^{4'}$ together with the carbon atom to which they are attached form: a) a 3- to 7-membered cycloalkyl ring optionally substituted by 1 to 5 R$^{14}$ moieties or -oxo; or b) a 3- to 7-membered cycloalkylether group having one oxygen atom optionally substituted by 1 to 5 R$^{14}$ moieties or oxo;

R$^6$, R$^{6'}$, R$^7$ and R$^{7'}$ are are independently selected from the group consisting of of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, aryl heterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, halo, —CH$_2$—O—Si(R$^9$)(R$^{10}$)(R$^{19}$), —SH, —CN, —OR$^9$, —C(O)R$^8$, —C(O)OR$^9$, —C(O)N(R$^{11}$)(R$^{12}$), —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S(O)R$^{10}$, —N(R$^{11}$)S(O)$_2$R$^{10}$—, —N(R$^{11}$)C(O)N(R$^{12}$)(R$^{13}$), —N(R$^{11}$)C(O)OR$^9$ and —C(=NOH)R$^8$;

or R$^6$, R$^{6'}$, R$^7$ and R$^{7'}$ together with the carbon atom to which they are attached form: a) a 3- to 7-membered cycloalkyl ring optionally substituted by 1 to 5 R$^{14}$ moieties or oxo; or b) a 3- to 7-membered cycloalkylether group having one oxygen atom optionally substituted by 1 to 5 R$^{14}$ moieties and/or oxo;

and optionally: i) R$^3$ and R$^4$ together with the carbon atom to which they are attached; ii) R$^{3'}$ and R$^{4'}$ together with the carbon atom to which they are attached; iii) R$^6$ and R$^7$ together with the carbon atom to which they are attached, or iv) or R$^{6'}$ and R$^{7'}$ together with the carbon atom to which they are attached, form one of the following multicyclic groups:

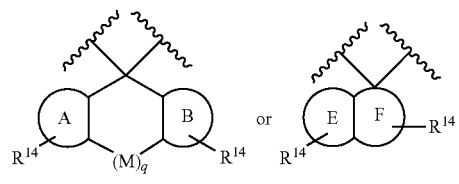

wherein:

M is independently —(CH$_2$)—, —S—, —N(R$^{19}$)—, —O—, —S(O)—, —S(O)$_2$—, or —C(O)—;

q is 0, 1, or 2;

A and B are independently aryl, heteroaryl, cycloalkyl, cycloalkenyl or heterocyclyl;

E is aryl or heteroaryl; and

F is cycloalkyl, cycloalkenyl, heterocyclyl or heterocyclenyl provided that i) R$^3$ and R$^4$; ii) R$^{3'}$ and R$^{4'}$; iii) R$^6$ and R$^7$; and iv) R$^{6'}$ and R$^{7'}$ cannot be combined to form said multicyclic groups:

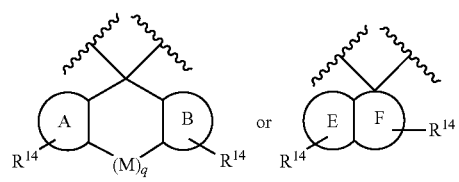

at the same time; preferably, i) R$^3$ and R$^4$ together with the carbon atom to which they are attached; ii) R$^{3'}$ and R$^{4'}$ together with the carbon atom to which they are attached; iii) R$^6$ and R$^7$ together with the carbon atom to which they are attached, or iv) or R$^{6'}$ and R$^{7'}$ together with the carbon atom to which they are attached, form one of the following multicyclic groups

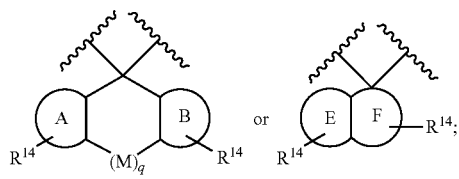

wherein
M is —CH₂—, —S—, —N(R¹⁹)—, —O—, —CH₂—CH₂—, —CH=CH—, —CH₂—S—, —CH₂—O—, —O—CH₂—, —S—CH₂—, —CH₂—N(R¹⁹)— or —N(R¹⁹)—CH₂—

A and B are independently aryl or heteroaryl,
q is 0 or 1,
provided that i) R³ and R⁴; ii) R³' and R⁴'; iii) R⁶ and R⁷; and iv) R⁶' and R⁷' cannot be combined to form said multicyclic groups:

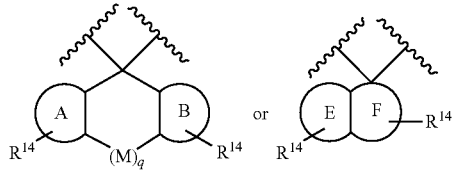

at the same time;

R⁸ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, —OR¹⁵, —N(R¹⁵)(R¹⁶), —N(R¹⁵)C(O)R¹⁶, —N(R¹⁵)S(O)R¹⁶, —N(R¹⁵)S(O)₂R¹⁶, —N(R¹⁵)S(O)₂N(R¹⁶)(R¹⁷), —N(R¹⁵)S(O)N(R¹⁶)(R¹⁷), —N(R¹⁵)C(O)N(R¹⁶)(R¹⁷) and —N(R¹⁵)C(O)OR¹⁶;

R⁹ is independently selected from the group consisting of H, alkyl, alkenyl, alkynyl, cycloalkyl, cycloalkylalkyl, heterocycloalkyl, heterocycloalkylalkyl, aryl, arylalkyl, heteroaryl and heteroarylalkyl;

R¹⁰ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl and —N(R¹⁵)(R¹⁶);

R¹¹, R¹² and R¹³ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, —C(O)R⁸, —C(O)OR⁹, —S(O)R¹⁰, —S(O)₂R¹⁰, —C(O)N(R¹⁵)(R¹⁶), —S(O)N(R¹⁵)(R¹⁶), and —S(O)₂N(R¹⁵)(R¹⁶);

R¹⁴ is 1-5 substituents independently selected from the group consisting of H, alkyl, alkenyl; alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —OR¹⁵, —C(O)R¹⁵, —C(O)OR¹⁵, —C(O)N(R¹⁵)(R¹⁶), —SR¹⁵, —S(O)N(R¹⁵)(R¹⁶), —S(O)₂N(R¹⁵)(R¹⁶), —C(=NOR¹⁵)R¹⁶, —P(O)(OR¹⁵)(OR¹⁶), —N(R¹⁵)(R¹⁶), —N(R¹⁵)C(O)R¹⁶, —N(R¹⁵)S(O)R¹⁶, —N(R¹⁵)S(O)₂R¹⁶, —N(R¹⁵)S(O)₂N(R¹⁶)(R¹⁷), —N(R¹⁵)S(O)N(R¹⁶)(R¹⁷), —N(R¹⁵)C(O)N(R¹⁶)(R¹⁷) and —N(R¹⁵)C(O)OR¹⁶;

R¹⁵, R¹⁶ and R¹⁷ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, arylheterocycloalkyl, R¹⁸-alkyl, R¹⁸-cycloalkyl, R¹⁸-cycloalkylalkyl, R¹⁸-heterocycloalkyl, R¹⁸-heterocycloalkylalkyl, R¹⁸-aryl, R¹⁸-arylalkyl, R¹⁸-heteroaryl and R¹⁸-heteroarylalkyl; or R¹⁵, R¹⁶ and R¹⁷ are

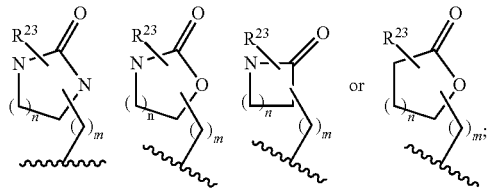

wherein R²³ numbers 0 to 5 substituents, m is 0 to 6 and n is 1 to 5;

R¹⁸ is 1-5 substituents independently selected from the group consisting of alkyl, alkenyl, alkynyl, aryl, arylalkyl, arylalkenyl, arylalkynyl, —NO₂, halo, heteroaryl, HO-alkyoxyalkyl, —CF₃, —CN, alkyl-CN, —C(O)R¹⁹, —C(O)OH, —C(O)OR¹⁹, —C(O)NHR²⁰, —C(O)NH₂, —C(O)NH₂—C(O)N(alkyl)₂, —C(O)N(alkyl)(aryl), —C(O)N(alkyl)(heteroaryl), —SR¹⁹, —S(O)₂R²⁰, —S(O)NH₂, —S(O)NH(alkyl), —S(O)N(alkyl)(alkyl), —S(O)NH(aryl), —S(O)₂NH₂, —S(O)₂NHR¹⁹, —S(O)₂NH(heterocycloalkyl), —S(O)₂N(alkyl)₂, —S(O)₂N(alkyl)(aryl), —OCF₃, —OH, —OR²⁰, —O-heterocycloalkyl, —O-cycloalkylalkyl, —O-heterocycloalkylalkyl, —NH₂, —NHR²⁰, —N(alkyl)₂, —N(arylalkyl)₂, —N(arylalkyl)-(heteroarylalkyl), —NHC(O)R²⁰, —NHC(O)NH₂, —NHC(O)NH(alkyl), —NHC(O)N(alkyl)(alkyl), —N(alkyl)C(O)NH(alkyl), —N(alkyl)C(O)N(alkyl)(alkyl), —NHS(O)₂R²⁰, —NHS(O)₂NH(alkyl), —NHS(O)₂N(alkyl)(alkyl), —N(alkyl)S(O)₂NH(alkyl) and —N(alkyl)S(O)₂N(alkyl)(alkyl);

or two R¹⁸ moieties on adjacent carbons can be linked together to form

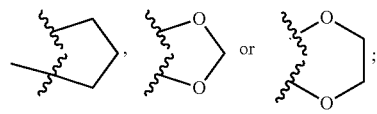

R¹⁹ is alkyl, alkenyl, alkynyl, cycloalkyl, aryl, arylalkyl or heteroarylalkyl;

R²⁰ is alkyl, alkenyl, alkynyl, cycloalkyl, aryl, halo substituted aryl, arylalkyl, heteroaryl or heteroarylalkyl; and wherein:
i) each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, heterocycloalkenylaryl, in R¹, R², R³, R³', R⁴, R⁴', R⁵, R⁶, R⁶', R⁷ and R⁷'; and
ii) each of the alkyl, cycloalkyl, cycloalkylalkyl, cycloalkenyl, arylcycloalkyl, heterocycloalkyl, heterocycloalkylalkyl, aryl, arylalkyl, heteroaryl, heteroarylalkyl, alkenyl and alkynyl groups in R, $R^8$, $R^9$, $R^{10}$, $R^{11}$, $R^{12}$, $R^{13}$ and $R^{14}$
are independently unsubstituted or substituted by 1 to 5 $R^{21}$ groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkyl heteroaryl, heterocycloalkylheteroaryl, cycloalkenylaryl, heterocycloalkenylaryl, halo, —CN, —$OR^{15}$, —C(O)$R^{15}$, —C(O)O$R^{15}$, —C(O)N($R^{15}$)($R^{16}$), —$SR^{15}$, —S(O)N($R^{15}$)($R^{16}$), —CH($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —CH$_2$—N($R^{15}$)C(O)$R^{16}$, —CH$_2$—N($R^{15}$)C(O)N($R^{16}$)($R^{17}$), —CH$_2$—$R^{15}$, —CH$_2$N($R^{15}$)($R^{16}$), —N($R^{15}$)S(O)$R^{16}$, —N($R^{15}$)S(O)$_2R^{16}$, —CH$_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —CH$_2$—N($R^{15}$)C(O)N($R^{16}$)($R^{17}$), —N($R^{15}$)C(O)O$R^{16}$, —CH$_2$—N($R^{15}$)C(O)O$R^{16}$, —S(O)$R^{15}$, —N$_3$, —NO$_2$ and —S(O)$_2R^{15}$; and wherein each of the alkyl, cycloalkenyl, cycloalkyl, cycloalkylalkyl, heterocycloalkyl, heterocycloalkylalkyl, aryl, arylalkyl, heteroaryl, heteroarylalkyl, alkenyl and alkynyl groups in $R^{21}$ are independently unsubstituted or substituted by 1 to 5 $R^{22}$ groups independently selected from the group consisting of alkyl, alkenyl, alkynyl, cycloalkyl, cycloalkenyl, heterocycloalkyl, aryl, heteroaryl, halo, —CF$_3$, —CN, —O$R^{15}$, —C(O)$R^{15}$, —C(O)O$R^{15}$, -alkyl-C(O)O$R^{15}$, C(O)N($R^{15}$)($R^{16}$), —S$R^{15}$, —S(O)N($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —CH$_2$—N($R^{15}$)C(O)$R^{16}$, —N($R^{15}$)S(O)$R^{16}$, —N($R^{15}$)S(O)$_2R^{16}$, —CH$_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —CH$_2$—N($R^{15}$)C(O)N($R^{16}$)($R^{17}$), —N($R^{15}$)C(O)O$R^{16}$, —CH$_2$—N($R^{15}$)C(O)O$R^{16}$, —N$_3$, —NO$_2$, —S(O)$R^{15}$ and —S(O)$_2R^{15}$;
or two $R^{21}$ or two $R^{22}$ moieties on adjacent carbons can be linked together to form

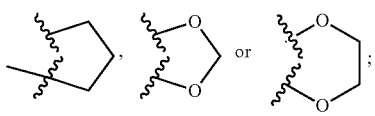

and when $R^{21}$ or $R^{22}$ are selected from the group consisting of —C(=NO$R^{15}$)$R^{16}$, —N($R^{15}$)C(O)$R^{16}$, —CH$_2$—N($R^{15}$)C(O)$R^{16}$, —N($R^{15}$)S(O)$R^{16}$, —N($R^{15}$)S(O)$_2R^{16}$, —CH$_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —CH$_2$—N($R^{15}$)C(O)N($R^{16}$)($R^{17}$), —N($R^{15}$)C(O)O$R^{16}$ and —CH$_2$—N($R^{15}$)C(O)O$R^{16}$, $R^{15}$ and $R^{16}$ together can be a $C_2$ to $C_4$ chain wherein, optionally, one, two or three ring carbons can be replaced by —C(O)— or —N(H)— and $R^{15}$ and $R^{16}$, together with the atoms to which they are attached, form a 5 to 7 membered ring, optionally substituted by $R^{23}$;

$R^{23}$ is 1 to 5 groups independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —O$R^{24}$, —C(O)$R^{24}$, —C(O)O$R^{24}$, —C(O)N($R^{24}$)($R^{25}$), —S$R^{24}$, —S(O)N($R^{24}$)($R^{25}$), —S(O)$_2$N($R^{24}$)($R^{25}$), —C(=NO$R^{24}$)$R^{25}$, —P(O)(O$R^{24}$)(O$R^{25}$), —N($R^{24}$)($R^{25}$), -alkyl-N($R^{24}$)($R^{25}$), —N($R^{24}$)C(O)$R^{25}$, —CH$_2$—N($R^{24}$)C(O)$R^{25}$, —N($R^{24}$)S(O)$R^{25}$, —N($R^{24}$)S(O)$_2R^{25}$, —CH$_2$—N($R^{24}$)S(O)$_2R^{25}$, —N($R^{24}$)S(O)$_2$N($R^{25}$)($R^{26}$), —N($R^{24}$)S(O)N($R^{25}$)($R^{26}$), —N($R^{24}$)C(O)N($R^{25}$)($R^{26}$), —CH$_2$—N($R^{24}$)C(O)N($R^{25}$)($R^{26}$), —N($R^{24}$)C(O)O$R^{25}$, —CH$_2$—N($R^{24}$)C(O)O$R^{25}$, —S(O)$R^{24}$ and —S(O)$_2R^{24}$; and wherein each of the alkyl, cycloalkyl, cycloalkylalkyl, heterocycloalkyl, heterocycloalkylalkyl, aryl, arylalkyl, heteroaryl, heteroarylalkyl, alkenyl and alkynyl groups in $R^{23}$ are independently unsubstituted or substituted by 1 to 5 $R^{27}$ groups independently selected from the group consisting of alkyl, cycloalkyl, heterocycloalkyl, aryl, heteroaryl, halo, —CF$_3$, —CN, —O$R^{24}$, —C(O)$R^{24}$, —C(O)O$R^{24}$, alkyl-C(O)O$R^{24}$, C(O)N($R^{24}$)($R^{25}$), —S$R^{24}$, —S(O)N($R^{24}$)($R^{25}$), —S(O)$_2$N($R^{24}$)($R^{25}$), —C(=NO$R^{24}$)$R^{25}$, —P(O)(O$R^{24}$)(O$R^{25}$)—N($R^{24}$)($R^{25}$)-alkyl-N($R^{24}$)($R^{25}$), —N($R^{24}$)C(O)$R^{25}$, —CH$_2$—N($R^{24}$)C(O)$R^{25}$, —N($R^{24}$)S(O)$R^{25}$, —N($R^{24}$)S(O)$_2R^{25}$, —CH$_2$—N($R^{24}$)S(O)$_2R^{25}$, —N($R^{24}$)S(O)$_2$N($R^{25}$)($R^{26}$), —N($R^{24}$)S(O)N($R^{25}$)($R^{26}$), —N($R^{24}$)C(O)N($R^{25}$)($R^{26}$), —CH$_2$—N($R^{24}$)C(O)N($R^{25}$)($R^{26}$), —N($R^{24}$)C(O)O$R^{25}$, —CH$_2$—N($R^{24}$)C(O)O$R^{25}$, —S(O)$R^{24}$ and —S(O)$_2R^{24}$;

$R^{24}$, $R^{25}$ and $R^{26}$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, $R^{27}$-alkyl, $R^{27}$-cycloalkyl, $R^{27}$-cycloalkylalkyl, $R^{27}$-heterocycloalkyl, $R^{27}$-heterocycloalkylalkyl, $R^{27}$-aryl, $R^{27}$-arylalkyl, $R^{27}$-heteroaryl and $R^{27}$-heteroarylalkyl;

$R^{27}$ is 1-5 substituents independently selected from the group consisting of alkyl, alkenyl, alkynyl, aryl, arylalkyl, —NO$_2$, halo, —CF$_3$, —CN, alkyl-CN, —C(O)$R^{28}$, —C(O)OH, —C(O)O$R^{28}$, —C(O)NH$R^{29}$, —C(O)N(alkyl)$_2$, —C(O)N(alkyl)(aryl), —C(O)N(alkyl)(heteroaryl), —S$R^{28}$, —S(O)$_2R^{29}$, —S(O)NH$_2$, —S(O)NH(alkyl), —S(O)N(alkyl)(alkyl), —S(O)NH(aryl), —S(O)$_2$NH$_2$, —S(O)$_2$NH$R^{28}$, —S(O)$_2$NH(aryl), —S(O)$_2$NH(heterocycloalkyl), —S(O)$_2$N(alkyl)$_2$, —S(O)$_2$N(alkyl)(aryl), —OH, —O$R^{29}$, —O-heterocycloalkyl, —O-cycloalkylalkyl, —O-heterocycloalkylalkyl, —NH$_2$, —NH$R^{29}$, —N(alkyl)$_2$, —N(arylalkyl)$_2$, —N(arylalkyl)(heteroarylalkyl), —NHC(O)$R^{29}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{29}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

$R^{28}$ is alkyl, alkenyl, alkynyl, cycloalkyl, arylalkyl or heteroarylalkyl; and $R^{29}$ is alkyl, alkenyl, alkynyl, cycloalkyl, aryl, arylalkyl, heteroaryl or heteroarylalkyl.

In another aspect, the invention relates to a pharmaceutical composition comprising at least one compound of formula I and a pharmaceutically acceptable carrier.

In another aspect, the invention comprises the method of inhibiting aspartyl protease comprising administering at least one compound of formula I to a patient in need of such treatment.

More specifically, the invention comprises: the method of treating a cardiovascular disease such as hypertension, renal failure, or a disease modulated by renin inhibition; the method of treating Human Immunodeficiency Virus; the method of treating a cognitive or neurodegenerative disease such as Alzheimer's Disease; the method of inhibiting plasmepins I and II for treatment of malaria; the method of inhibiting Cathepsin D for the treatment of Alzheimer's Disease, breast cancer, and ovarian cancer; and the method of inhibiting protozoal enzymes, for example inhibition of plasmodium falciparnum, for the treatment of fungal infections. Said method of treatment comprise administering at least one compound of formula I to a patient in need of such treatment. In particular, the invention comprises the method of treating Alzheimer's disease comprising administering at least one compound of formula I to a patient in need of such treatment.

In another aspect, the invention comprises the method of treating Alzheimer's disease comprising administering to a patient I need of such treatment a combination of at least one compound of formula I and a cholinesterase inhibitor or a modulator of muscarinic receptors, such as, but not limited to, a muscarinic m2 antagonist or an m1 muscarinic agonist.

Another aspect of this invention is pharmaceutical composition comprising an effective amount of a compound of claim 1 and at least one second pharmaceutical agent selected from the group consisting of beta secretase inhibitors; gamma secretase inhibitors; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; and promoters of alpha secretase activity and methods of treating the disease states associated with this compounds.

In a final aspect, the invention relates to a kit comprising in separate containers in a single package pharmaceutical compositions for use in combination, in which one container comprises a compound of formula I in a pharmaceutically acceptable carrier and a second container comprises a cholinesterase inhibitor or a muscarinic antagonist in a pharmaceutically acceptable carrier, the combined quantities being an effective amount to treat a cognitive disease or neurodegenerative disease such as Alzheimer's disease.

DETAILED DESCRIPTION

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" protion of "hydroxyalkyl", "haloalkyl", "alkoxy" etc.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl, n-butyl, t-butyl, n-pentyl, heptyl, nonyl and decyl. $R^{32}$-substituted alkyl groups include fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl.

"Aryl" means an aromatic monocyclic or multicyclic ring system comprising about 6 to about 14 carbon atoms, preferably about 6 to about 10 carbon atoms. The aryl group can be optionally substituted with one or more substituents (e.g., $R^{18}$, $R^{21}R^{22}$, etc.) which may be the same or different, and are as defined herein or two substituents on adjacent carbons can be linked together to form

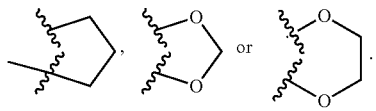

Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one to four of the ring atoms is an element other than carbon, for example nitrogen, oxygen or sulfur, alone or in combination. Preferred heteroaryls contain about 5 to about 6 ring atoms. The "heteroaryl" can be optionally substituted by one or more $R^{21}$ substituents which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more $R^{21}$ substituents which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. Further non-limiting examples of cycloalkyl include the following

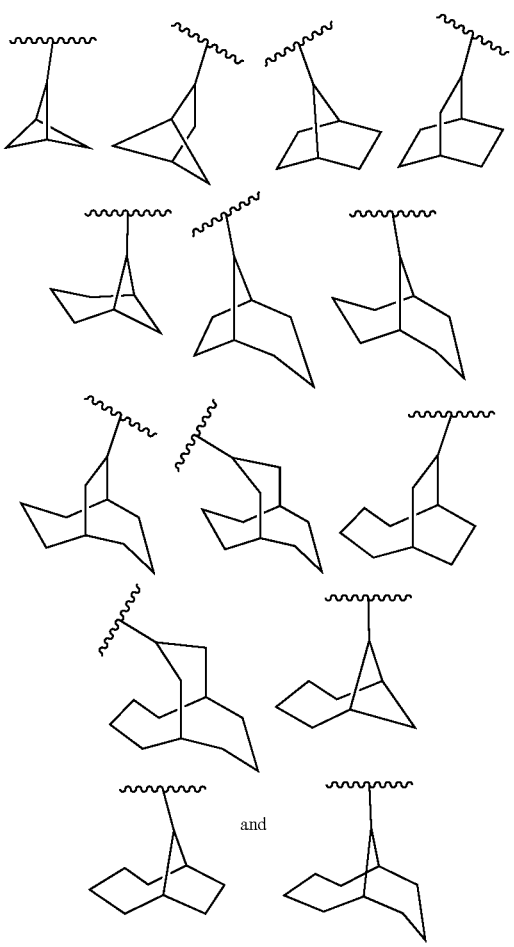

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkenyl" means a non-aromatic mono or multicyclic ring system comprising about 3 to about 10 carbon atoms, preferably about 5 to about 10 carbon atoms which contains at least one carbon-carbon double bond. The cycloalkenyl ring can be optionally substituted with one or more $R^{21}$ substituents which may be the same or different, and are as defined above. Preferred cycloalkenyl rings contain about 5 to about 7 ring atoms. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" (or "heterocycloalkeneyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4- tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Halo" means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl is replaced by a halo group defined above.

"Heterocyclyl" (or heterocycloalkyl) means a non-aromatic saturated monocyclic or multicyclic ring system comprising about 3 to about 10 ring atoms, preferably about 5 to about 10 ring atoms, in which 1-3, preferably 1 or 2 of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more $R^{21}$ substituents which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Arylcycloalkyl" means a group derived from a fused aryl and cycloalkyl as defined herein. Preferred arylcycloalkyls are those wherein aryl is phenyl and cycloalkyl consists of about 5 to about 6 ring atoms. The arylcycloalkyl can be optionally substituted by 1-5 $R^{21}$ substituents. Non-limiting examples of suitable arylcycloalkyls include indanyl and 1,2,3,4-tetrahydronaphthyl and the like. The bond to the parent moiety is through a non-aromatic carbon atom.

"Arylheterocycloalkyl" means a group derived from a fused aryl and heterocycloalkyl as defined herein. Preferred arylcycloalkyls are those wherein aryl is phenyl and heterocycloalkyl consists of about 5 to about 6 ring atoms. The arylheterocycloalkyl can be optionally substituted by 1-5 $R^{21}$ substituents. Non-limiting examples of suitable arylheterocycloalkyls include

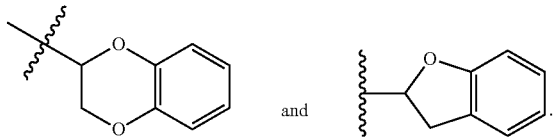

The bond to the parent moiety is through a non-aromatic carbon atom.

Similarly, "heteroarylalkyl" "cycloalkylalkyl" and "heterocycloalkylalkyl" mean a heteroaryl-, cycloalkyl- or heterocycloalkyl-alkyl- group in which the heteroaryl, cycloalkyl, heterocycloalkyl and alkyl are as previously described. It is also understood that the terms "arylcycloalkylalkyl", "heteroarylcycloalkylalkyl", "arylheterocycloalkylalkyl", "heteroarylheterocycloalkylalkyl", "heteroarylcycloalkyl", "heteroarylheterocycloalkyl", "arylcycloalkenyl", "heteroarylcycloalkenyl", "heterocycloalkenyl", "arylheterocycloalkenyl", "heteroarylheterocycloalkenyl", "cycloalkylaryl", "heterocycloalkylaryl", "heterocycloalkenylaryl", "heterocycloalkylheteroaryl", "cycloalkenylaryl" and "heterocycloalkenylaryl" similarly represented by the combination of the groups aryl-, cycloalkyl-, alkyl-, heteroaryl-, heterocycloalkyl-, cycloalkenyl- and heterocycloalkenyl- as previously described Preferred groups contain a lower alkyl group. The bond to the parent moiety is through the alkyl.

"Acyl" means an H—C(O)—, alkyl-C(O)—, alkenyl-C(O)—, alkynyl-C(O)—, aryl-C(O)— or cycloalkyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Alkyoxyalkyl" means a group derived from an alkoxy and alkyl as defined herein. The bond to the parent moiety is through the alkyl.

"Arylalkenyl" means a group derived from an aryl and alkenyl as defined herein. Preferred arylalkenyls are those wherein aryl is phenyl and the alkenyl consists of about 3 to about 6 atoms. The arylalkenyl can be optionally substituted by one or more $R^{27}$ substituents. The bond to the parent moiety is through a non-aromatic carbon atom.

"Arylalkynyl" means a group derived from a aryl and alkynyl as defined herein. Preferred arylalkynyls are those wherein aryl is phenyl and the alkynyl consists of about 3 to about 6 atoms. The arylalkynyl can be optionally substituted by one or more $R^{27}$ substituents. The bond to the parent moiety is through a non-aromatic carbon atom.

The suffix "ene" on alkyl, aryl, hetercycloalkyl, etc. indicates a divalent moiety, e.g., —$CH_2CH_2$— is ethylene, and

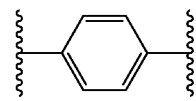

is para-phenylene.

The term "optionally substituted" means optional substitution with the specified groups, radicals or moieties, in available position or positions.

Substitution on a cycloalkylalkyl, heterocycloalkylalkyl, arylalkyl, or heteroarylalkyl moiety includes substitution on the ring portion and/or on the alkyl portion of the group.

When a variable appears more than once in a group, e.g., $R^8$ in —$N(R^8)_2$, or a variable appears more than once in the structure of formula I, e.g., $R^{15}$ may appear in both $R^1$ and $R^3$, the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of formula I," one to three compounds of formula I can be administered at the same time, preferably one.

As used herein, the term "composition" is intended to encompass a product comprising the specified ingredients in the specified amounts, as well as any product which results, directly or indirectly, from combination of the specified ingredients in the specified amounts.

The wavy line ⁓⁓⁓ as a bond generally indicates a mixture of, or either of, the possible isomers, e.g., containing (R)— and (S)— stereochemistry. For example,

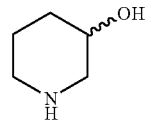

means containing both

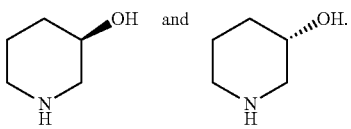

Lines drawn into the ring systems, such as, for example:

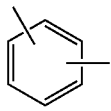

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, or heterocyclenyl ring, e.g.,

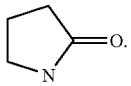

The line ----- indicates a single or double bond that may form between X and Y. The variables R, $R^6$, $R^{6'}$, $R^7$ and $R^{7'}$ may be present or absent in order to satisfy the valencies.

It is noted that the carbons of formula I may be replaced with 1 to 3 silicon atoms so long as all valency requirements are satisfied.

In this specification, where there are multiple oxygen and/or sulfur atoms in a ring system, there cannot be any adjacent oxygen and/or sulfer present in said ring system.

As well known in the art, a bond drawn from a particular atom wherein no moiety is depicted at the terminal end of the bond indicates a methyl group bound through that bond to the atom, unless stated otherwise. For example:

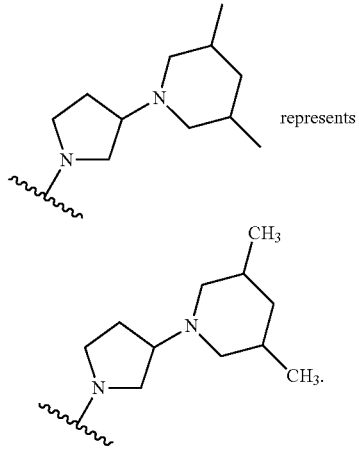

represents

It should also be noted that any heteroatom with unsatisfied valences in the text, schemes, examples, structural formulae, and any Tables herein is assumed to have the hydrogen atom or atoms to satisfy the valences.

Those skilled in the art will recognize that certain compounds of formula I are tautomeric, and all such tautomeric forms are contemplated herein as part of the present invention.

When $R^{21}$ and $R^{22}$, are, for example, —N($R^{15}$)C(O)N($R^{16}$)($R^{17}$) and $R^{15}$ and $R^{16}$ form a ring, the moiety formed, is, for example,

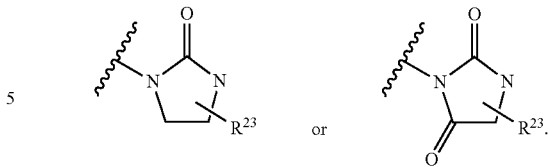

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-(C1-C2)alkyl and piperidino-, pyrrolidino- or morpholino($C_2$-$C_3$)alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N-($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$)alkyl, carboxy ($C_1$-$C_6$)alkyl, amino ($C_1$-$C_4$)alkyl or mono-N— or di-N,N-($C_1$-$C_6$)alkylaminoalkyl, —C($Y^4$)$Y^5$ wherein $Y^4$ is H or methyl and $Y^5$ is mono-N— or di-N,N-($C_1$-$C_6$)alkylamino morpholino, piperidin-1-yl or pyrrolidin-1-yl, and the like.

The compounds of formula I may exists in unsolvated as well as solvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting aspartyl protease and/or inhibiting BACE-1 and thus producing the desired therapeutic effect in a suitable patient.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. For example, if a compound of Formula (I) incorporates a double bond or a fused ring, both the cis- and trans-forms, as well as mixtures, are embraced within the scope of the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

Polymorphic forms of the compounds of formula I, and of the salts, solvates and prodrugs of the compounds of formula I, are intended to be included in the present invention The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$ $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

It should be noted that throughout the specification and Claims appended hereto any formula, compound, moiety or chemical illustration with unsatisfied valences is assumed to have the hydrogen atom to satisfy the valences unless the context indicates a bond.

Compounds of formula I wherein the variables are as defined above include the following independently preferred structures:

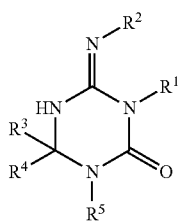

IA

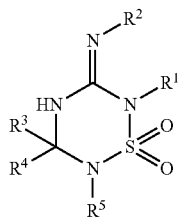

IB

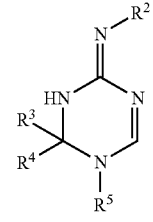

IC

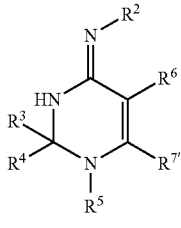

ID

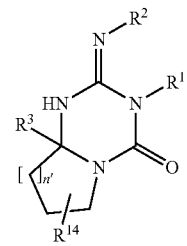

IE

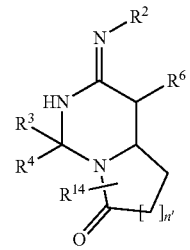

IF

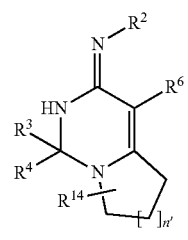

IG

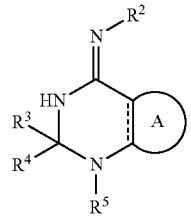

IH

In structures IE, IF and IG, n' is preferably an interger between 0 and 3. In structure IH, ring A is a 5- to 7-membered cycloalkyl, cycloalkenyl, heterocycyl, heterocyclenyl, aryl or heteroaryl ring having 0 to 3 heteroatoms selected from the group consisting of O, N,N(R) and S, wherein said rings are optionally substituted by 1 to 5 independently selected $R^{14}$ moieties and/or by oxo when said rings are cycloalkyl, cycloalkenyl, heterocyclyl or heterocyclenyl;

Another group of preferred compounds of formula I is that wherein $R^2$ is H $R^3$, $R^4$, $R^6$ and $R^7$ are preferably selected from the group consisting of alkyl, cycloalkyl, cycloalkylalkyl, heterocycloalkyl, heterocycloalkylalkyl, aryl, arylalkyl, heteroaryl, heteroarylalkyl, —CH$_2$—O—Si($R^9$)($R^{10}$)($R^{19}$), —CN, —C(O)$R^8$, —C(O)O$R^9$, —C(O)N($R^{11}$)($R^{12}$), —S$R^{19}$, —S(O)N($R^{11}$)($R^{12}$), —S(O)$_2$N($R^{11}$)($R^{12}$), —N($R^{11}$)($R^{12}$), —N($R^{11}$)C(O)$R^8$, —N($R^{11}$)S(O)$R^{10}$, —N($R^{11}$)C(O)N($R^{12}$)($R^{13}$), —N($R^{11}$)C(O)O$R^9$ and —C(=NOH)$R^8$.

$R^3$, $R^4$, $R^6$ and $R^7$ are preferably selected from the group consisting of aryl, heteroaryl, heteroarylalkyl, arylalkyl, cycloalkyl, heterocycloalkyl, heterocycloalkylalkyl, alkyl and cycloalkylalkyl.

In a group of preferred compounds
X is NR$^1$
Y is —C(O)—;

R¹ is H, alkyl, preferably methyl, $R^{21}$-alkyl, preferably —$CH_2CF_3$, cycloalkyl, preferably cyclopropyl, arylalkyl, $R^{21}$-arylalkyl, cycloalkylalkyl, $R^{21}$-cycloalkylalkyl, heterocycloalkyalkyl or $R^{21}$-heterocycloalkylalkyl, R² is H;

R³ is alkyl, cycloalkylalkyl, cycloalkyl, aryl, arylalkyl, $R^{21}$-alkyl, $R^{21}$-cycloalkylalkyl, $R^{21}$-cycloalkyl, $R^{21}$-aryl, $R^{21}$-arylalkyl, $R^{21}$-heterocyclyl or $R^{21}$-heteroaryl;

R⁴ is alkyl, cycloalkylalkyl, cycloalkyl, aryl, arylalkyl, $R^{21}$-alkyl, $R^{21}$-cycloalkylalkyl, $R^{21}$-cycloalkyl, $R^{21}$-aryl, $R^{21}$-arylalkyl, $R^{21}$-heterocyclyl or $R^{21}$-heteroaryl;

R⁵ is H, alkyl, $R^{21}$-alkyl, cycloalkyl, aryl, arylalkyl, $R^{21}$-arylalkyl, cycloalkylalkyl, $R^{21}$-cycloalkylalkyl, heteroaryl, heteroarylalkyl, heterocycloalkyalkyl or $R^{21}$-heterocycloalkylalkyl;

R⁶ is alkyl, cycloalkylalkyl, cycloalkyl, aryl, arylalkyl, $R^{21}$-alkyl, $R^{21}$-cycloalkylalkyl, $R^{21}$-cycloalkyl, $R^{21}$-aryl or $R^{21}$-arylalkyl;

R⁷ is alkyl, cycloalkylalkyl, cycloalkyl, aryl, arylalkyl, $R^{21}$-alkyl, $R^{21}$-cycloalkylalkyl, $R^{21}$-cycloalkyl, $R^{21}$-aryl or $R^{21}$-arylalkyl;

$R^{15}$, $R^{16}$ and $R^{17}$ is H, $R^{18}$-alkyl, alkyl or $R^{21}$ is alkyl, aryl, halo, —$OR^{15}$, —$NO_2$, —$C(O)R^{15}$, —$CH_2$—$N(R^{15})C(O)N(R^{16})(R^{17})$ or —$CH(R^{15})(R^{16})$;

n is 1;

m is 1;

$R^{18}$ is —$OR^{20}$ $R^{20}$ is aryl;

and $R^{23}$ is alkyl.

In a group of preferred compounds

R¹ is H, $CH_3$, —$CH_2CF_3$, cyclopropyl, where T is $R''C(O)$—, $R''S(O)_2$, $R''NCO$— and n" is 1 to 4, where T is $R''C(O)$—, $R''S(O)_2$, $R''NCO$— and n" is 1 to 4, where R" is H, alkyl, arylalkyl, heteroarylalkyl, cycloalkylalkyl, heterocycloalkylalkyl, arylcycloalkylalkyl, heteroarylcycloalkylalkyl, aryl heterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl.

and

R³, R⁴, R⁶ and R⁷ are methyl, ethyl, cyclopropyl,

Preferred definitions for $R^{21}$ include alkyl, halo, phenyl, $R^{22}$-phenyl, where $R^{22}$ may be, for example, alkyl, halo or —$OR^{15}$.

In an additional group of preferred compounds;

X is —$N(CH_3)$;

Y is —$C(O)$—;

R⁵ is H, $CH_3$, or cyclopropyl;

R¹ is H, alkyl, preferably methyl, $R^{21}$-alkyl, preferably —$CH_2CF_3$, arylalkyl, $R^{21}$-arylalkyl, cycloalkylalkyl, $R^{21}$-cycloalkylalkyl, heterocycloalkyalkyl or $R^{21}$-heterocycloalkylalkyl, R² is H;

$R^3$ is alkyl, cycloalkylalkyl, cycloalkyl, aryl, arylalkyl, $R^{21}$-alkyl, $R^{21}$-cycloalkylalkyl, $R^{21}$-cycloalkyl, $R^{21}$-aryl, $R^{21}$-arylalkyl, heteroarylalkyl, heteroaryl, heterocycloalkyl, heterocycloalkylalkyl, $R^{21}$-heteroarylalkyl, $R^{21}$-heteroaryl, $R^{21}$-heterocycloalkyl or $R^{21}$-heterocycloalkylalkyl;

$R^4$ is alkyl, cycloalkylalkyl, cycloalkyl, aryl, arylalkyl, $R^{21}$-alkyl, $R^{21}$-cycloalkylalkyl, $R^{21}$-cycloalkyl, $R^{21}$-aryl, $R^{21}$-arylalkyl, heteroarylalkyl, heteroaryl, heterocycloalkyl, heterocycloalkylalkyl, $R^{21}$-heteroarylalkyl, $R^{21}$-heteroaryl, $R^{21}$-heterocycloalkyl or $R^{21}$-heterocycloalkylalkyl;

$R^5$ is H, alkyl, $R^{21}$-alkyl, arylalkyl, $R^{21}$-arylalkyl, cycloalkylalkyl, $R^{21}$-cycloalkylalkyl, heterocycloalkyalkyl or $R^{21}$-heterocycloalkylalkyl;

$R^6$ is alkyl, cycloalkylalkyl, cycloalkyl, aryl, arylalkyl, $R^{21}$-alkyl, $R^{21}$-cycloalkylalkyl, $R^{21}$-cycloalkyl, $R^{21}$-aryl, $R^{21}$-arylalkyl, heteroarylalkyl, heteroaryl, heterocycloalkyl, heterocycloalkylalkyl, $R^{21}$-heteroarylalkyl, $R^{21}$-heteroaryl, $R^{21}$-heterocycloalkyl or $R^{21}$-heterocycloalkylalkyl;

$R^7$ is alkyl, cycloalkylalkyl, cycloalkyl, aryl, arylalkyl, $R^{21}$-alkyl, $R^{21}$-cycloalkylalkyl, $R^{21}$-cycloalkyl, $R^{21}$-aryl, $R^{21}$-arylalkyl, heteroarylalkyl, heteroaryl, heterocycloalkyl, heterocycloalkylalkyl, $R^{21}$-heteroarylalkyl, $R^{21}$-heteroaryl, $R^{21}$-heterocycloalkyl or $R^{21}$-heterocycloalkylalkyl;

$R^{15}$, $R^{16}$ and $R^{17}$ is H, cycloalkyl, cycloalkylalkyl, $R^{18}$-alkyl, alkyl, aryl, $R^{18}$-aryl, $R^{18}$-arylalkyl, arylalkyl,

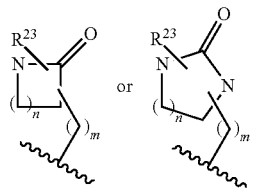

n is 1 or 2;

m is 0 or 1;

$R^{18}$ is —$OR^{20}$ or halo;

$R^{20}$ is aryl or halo substituted aryl;

$R^{21}$ is alkyl, aryl, heteroaryl, $R^{22}$-alkyl, $R^{22}$-aryl, $R^{22}$-heteroaryl, halo, heterocycloalkyl, —$N(R^{15})(R^{16})$, —$OR^{15}$, —$NO_2$, —$C(O)R^{15}$, —$N(R^{15})C(O)R^{16}$, —$N(R^{15})S(O)_2R^{16}$, —$CH_2$—$N(R^{15})C(O)N(R^{16})(R^{17})$, —$N(R^{15})C(O)N(R^{16})(R^{17})$ or —$CH(R^{15})(R^{16})$;

$R^{22}$ is —$OR^{15}$, halo, alkenyl, alkynyl, preferably —C≡C(CH$_3$), or —CN. and $R^{23}$ is H or alkyl.

More preferred compounds of the invention are those of formula

IA

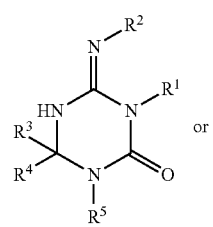

or

IB

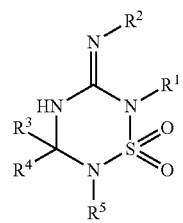

wherein $R^1$ is hydrogen, alkyl, preferably methyl, $R^{21}$-alkyl, preferably —$CH_2CF_3$, cycloalkyl, preferably cyclopropyl, $R^{21}$-cycloalkyl, arylalkyl, $R^{21}$-arylalkyl, heterocyclalkylalkyl, $R^{21}$-heterocyclalkyl, or $R^{21}$-arylalkyl;

$R^2$ is H;

$R^3$ is $R^{21}$-aryl;

$R^4$ is alkyl, $R^{21}$-alkyl, cycloalkyl, $R^{21}$-cycloalkyl, aryl or $R^{21}$-aryl; and $R^5$ is H, alkyl, cycloalkyl, aryl, heteroaryl, arylalkyl or heteroarylalkyl.

In the above definitions, compounds where $R^{21}$ is alkyl, cycloalkyl, heterocycloalkyl, $R^{23}$-heterocycloalkylalkyl, aryl, $R^{23}$-aryl, halo, —$OR^{15}$, —$N(R^{15})(R^{16})$, —$C(O)CR^{15}$ are a preferred embodiment.

Preferred embodiments of formula IH include compounds of formulae:

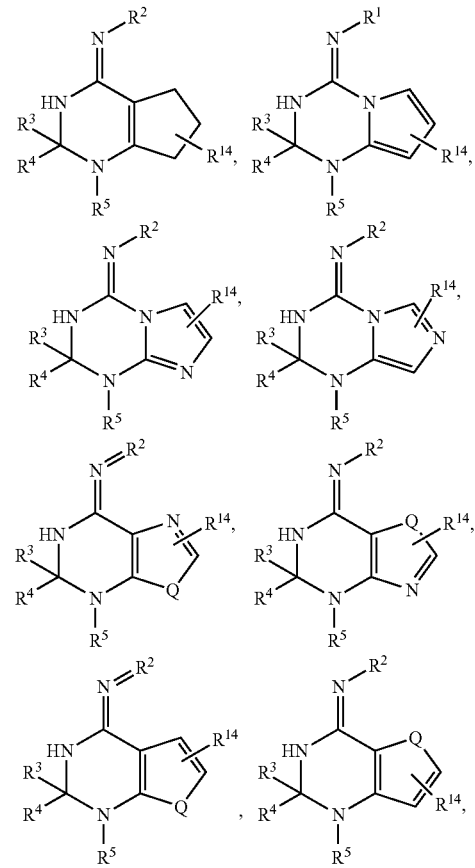

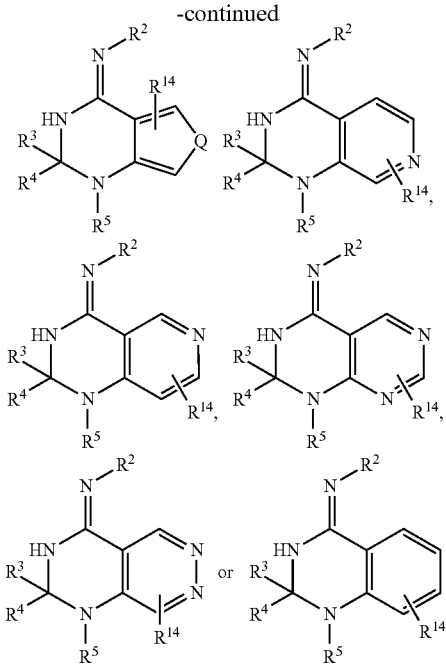

where $R^2$, $R^3$, $R^4$, $R^5$ and $R^{14}$ are defined above and Q is —O—, —NR— or —S—, where R is H or alkyl.

Other embodiments of formula I include compounds of formulae:

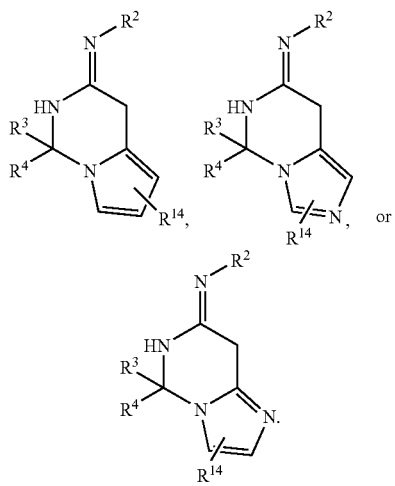

Another preferred embodiment are compounds of the formula:

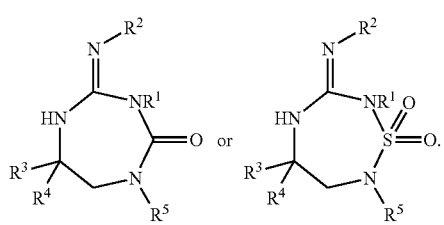

Compounds of formula I can be made using procedures known in the art. Preparative methods for preparing starting materials and compounds of formula I are show below as general reaction schemes followed by specific procedures, but those skilled in the art will recognize that other procedures can also be suitable. The particular process to be utilized in the preparation of the compounds of this invention depends upon the specific compound desired. Such factors as the selection of the specific moieties and the specific substituents on the various moieties all play a role in the synthetic route employed to prepare a specific compounds. These factors are well within the skill level of the practitioner.

For the synthesis of any particular compound, one skilled in the art will recognize that the use of protection groups may be required. A description of suitable protecting groups may be found in "Protective Goups in Organic Synthesis", $2^{nd}$ Ed., John Wiley and Sons, New York (1999) by T. W. Greene and P. G. M. Wuts. In the Schemes and in the Examples below, the following abbreviations are used:

methyl: Me;
ethyl: Et;
protecting group: PG
benzyl: bn
triphenyl phosphine: $Ph_3P$
alcohol: ROH (e.g., methanol, ethanol, etc.)
diphenylphosphoryl azide: DPPA
2,4-bis(4-methoxyphenyl)-1,3,2,4-dithiadiphosphetane-2,4-disufide: Lawesson's reagent.
liquid chromatography mass spectroscopy: LCMS
acetonitrile: MeCN
methanol: MeOH
ethanol: EtOH
room temperature: RT
dimethylforamide: DMF
acetic acid: AcOH
dichloromethane: DCM
tetrahydrofuran: THF
ethyl acetate: ETAc
preparative thin layer chromatography: prep TLC
hour: h
minutes: min
nuclear magnetic resonance: NMR
liquid chromatography mass spectrometry: LCMS
deuterated dimethyl sulfoxide: DMSO-d6
RT: retention time.

All NMR data are collected on 400 MHz NMR spectrometers unless otherwise indicated. LC-Electrospray-Mass spectroscopy with a C-18 column and 5% to 95% MeCN in water as the mobile phase is used to determine the molecular mass and retention time.

In general, the compounds in the invention may be produced by processes known to those skilled in the art and by known processes analogous thereto. The following reaction schemes serve as examples of these processes. In the reaction schemes described below to prepare specific embodiments. One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme and in the preparations and examples described below.

General Methods of Preparing Compounds of Formula I

In the following reaction schemes, each variable may be any moiety within that varible's definition.

The compounds of formulae IA and IC can be synthesized according to Reaction Scheme 1, which presents three alternative routes to make compounds of formula 1A. In the first route, compound 1, prepared using methods adapted from the one described in Ger. Offen, 10212054 (Oct. 2, 2003), is reacted with ketone $R^3C(O)R^4$ in the presence of and acid catalyst to form compounds of Formula 1A. Alternatively, compound 2, where $PG_1$ is an amine protecting group, is reacted with compound 3 to prepare compound 4, where X is a heteroatom, such as S or O, and R is a hydrocarbyl, cyclic hydrocarbyl or aromatic group (e.g., methyl, ethyl or phenyl) or RX may be halo (e.g., Cl or Br), which is then cyclized in the presence of base, such as triethylamine or NaH, while heating. A third route converts dithiobiuret 1 b to compound 2b by reaction with ketone $R^3COR^4$ and acid catalyst followed by the subsequent reaction with an oxidant such as $H_2O_2$ in water (see, T. Tsao et al, *Synthetic Comm.*, 22(11), 1597-1601 (1992)). Reacting 2b with $P_2S_5$ or Lawesson's reagent and aminolysis using $H_2O_2$ and amine $R^2NH_2$ provides compounds 1A Compounds of formula 1C can be prepared from the compounds of formula 1A by reacting these compounds with phosphorous oxychloride followed by reduction with hydrogen or a hydride source, such as LAH or $NaBH_4$.

The compounds of formula IB can be prepared according to Reaction Scheme 2. Compound 5, where PG is an amine protecting group, is reacted with compound 6 first in the presence of base, followed by ammonia to yield compound 7. Compound 7 is then reacted with ketone $R^3C(O)R^4$ in the presence of an acid catalyst to yield a compound of formula IB.

Reaction Scheme 2

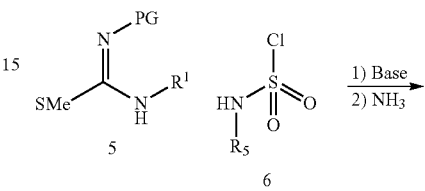

Reaction Scheme 1

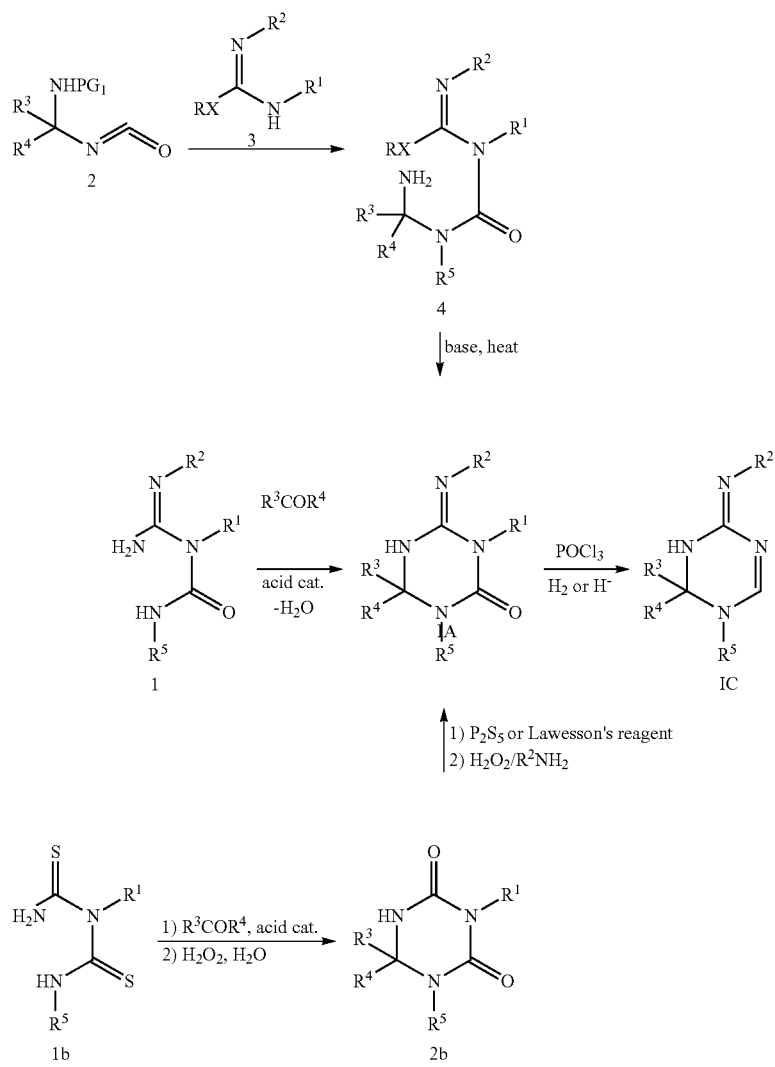

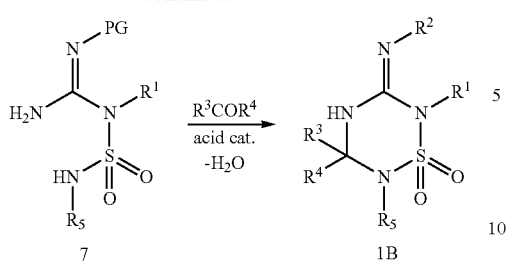
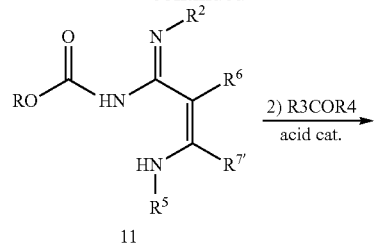
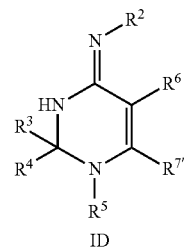

Reaction Scheme 3 depicts an alternative route to prepare compounds of formula 1C. In this process compound 8 is reacted with CH(OEt)$_3$ to yield compound 9. Compound 9 is then reacted with amine R$^5$NH$_2$ and ketone R$^3$C(O)R$^4$ in the presence of an acid catalyst to produce a compound of formula 1C.

Reaction Scheme 3

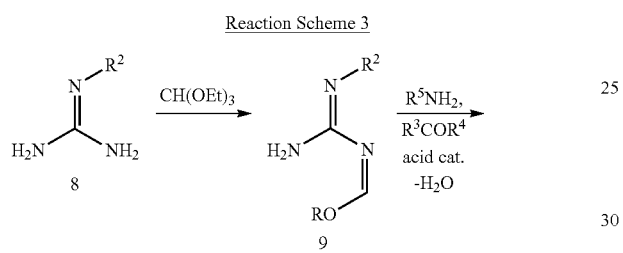

Compounds of Formula 1E can be prepared according to Reaction Scheme 5. Compound 12 can be prepared analogous to the procedure discussed in *Tetrahedron*, 53(27), 9233-9240 (1997). Reacting compound 12 with DPPA yields compound 13, which then is reacted with R$^2$N$_3$ and triphenylphosphine to yield compound 14. Compound 14 then is reacted with the amine R$^1$NH$_2$ to yield a compound of formula 1E.

Reaction Scheme 5

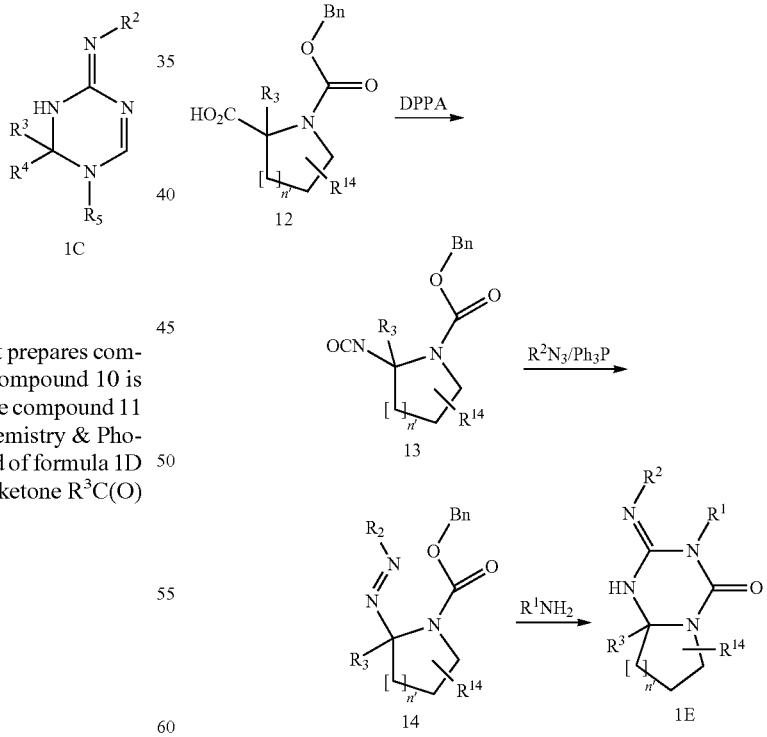

Reaction Scheme 4 illustrates a process that prepares compounds of formula 1D. The reaction where compound 10 is reacted with alcohol ROH to form intermediate compound 11 is described by Shaw and Shetlar in Phytochemistry & Photobiology 49(3), pp 267-71 (1989). Compound of formula 1D is formed by reacting compound 11 with the ketone R$^3$C(O)R$^4$ in the presence of an acid catalyst.

Reaction Scheme 4

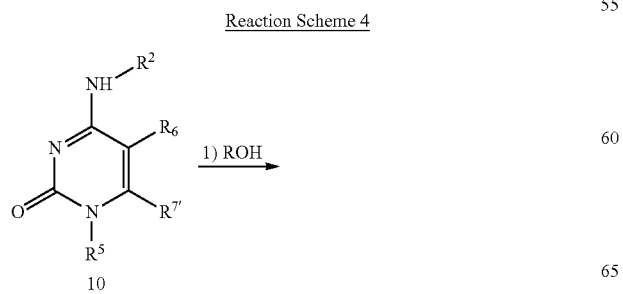

Compounds of Formula 1F can be prepared according to Reaction Scheme 6 by reacting compound 15, which can be prepared by following the procedure described by Muenster et al., *Tetrahedron: Asymmetry*, 6(11), pp. 2673-2674 (1995), with hydrogen sulfide and amine R$^2$NH$_2$ to form compound 16. Compound 16 is then reacted with ketone $R^3C(O)R^4$ in the presence of an acid catalyst.

Reaction Scheme 6

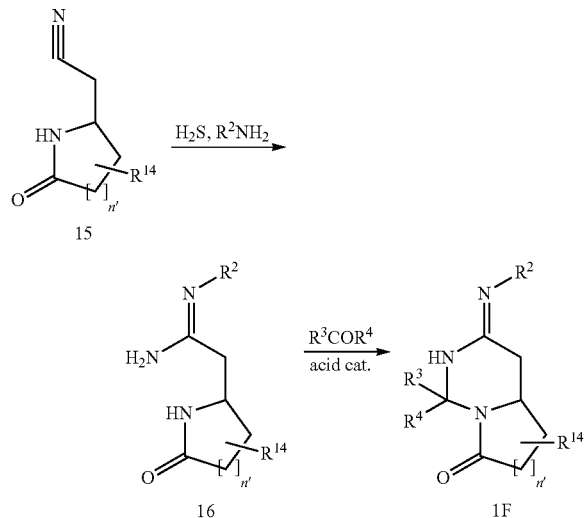

Reaction Scheme 7 outlines a process to prepare compounds of formula IG, wherein ring A is defined as above. Reacting starting material 17 with ketone $R^3C(O)R^4$ in the presence of an acid catalyst to produce intermediate 18. Compound 18 is reacted with Lawesson's reagent and methyl iodide to produce compound 18, which is then reacted with amine $R^2NH_2$ to yield 1G.

Reaction Scheme 7

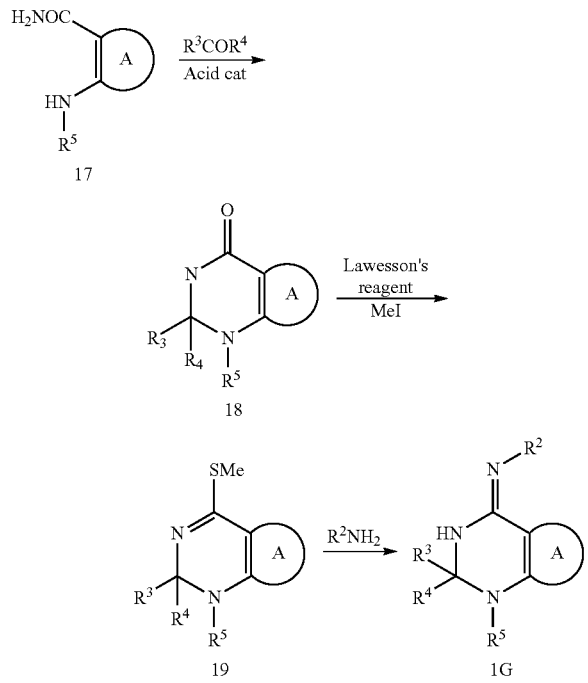

The following Preparative Examples are intended to illustrate, but not limit, the scope of the invention.

PREPARATIVE EXAMPLES

Compound Example 1

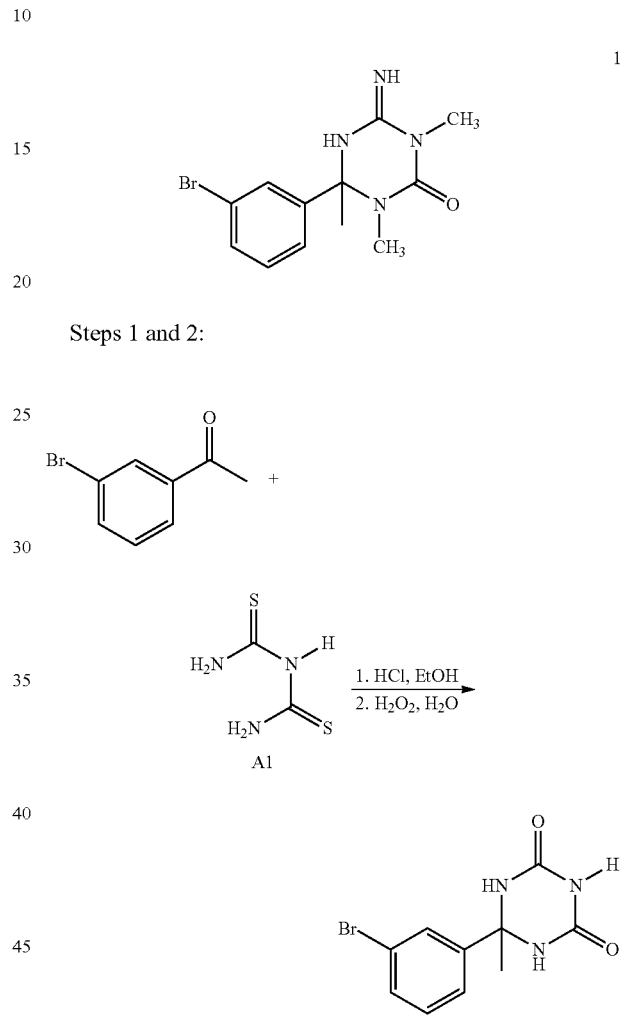

Steps 1 and 2:

Dithiobiuret A1 (1.35 g) was suspended in a solution of 3-bromo-acetophenone (2.19 g) in absolute EtOH (10 mL). HCl gas was bubbled into the reaction mixture for about 40 minutes to give first a clear yellow solution and then a white precipitate. The mixture was stirred at RT for 30 min., then excess 1 N NaOH was added and the reaction mixture was heated to 50 C. After 30 min., the mixture was cooled and neutralized with AcOH to collect a white solid by filtration (2.65 g). A portion of this solid (1.77 g) was dissolved in 2.5 N NaOH (9.74 mL) and heated to 40-45° C. for a short period, then cooled and 30% $H_2O_2$ (5.1 mL) added dropwise to maintain the reaction temperature at 40-45° C. After the addition was complete, the mixture was heated to 80° C. briefly then cooled to RT and neutralized with 2N $H_2SO_4$ to give A2 as a white solid (1.38 g).

Step 3:

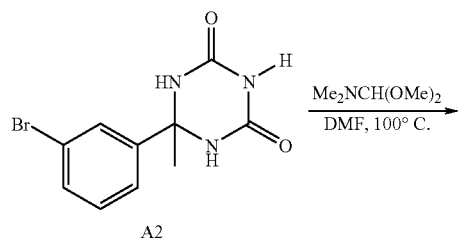

A2 (1.25 g) and DMF dimethyl acetal (1.18 mL) in DMF (15 mL) were heated to 100° C. for 1 hr then water was added (4 mL) and the mixture stirred for 30 min. and concentrated in vacuo to about 10 mL volume. The reaction mixture was then further diluted with water (40 mL) to give a solid which was collected by filtration and triturated with DCM to give compound A3 as a light tan solid (0.46 g).

Step 4:

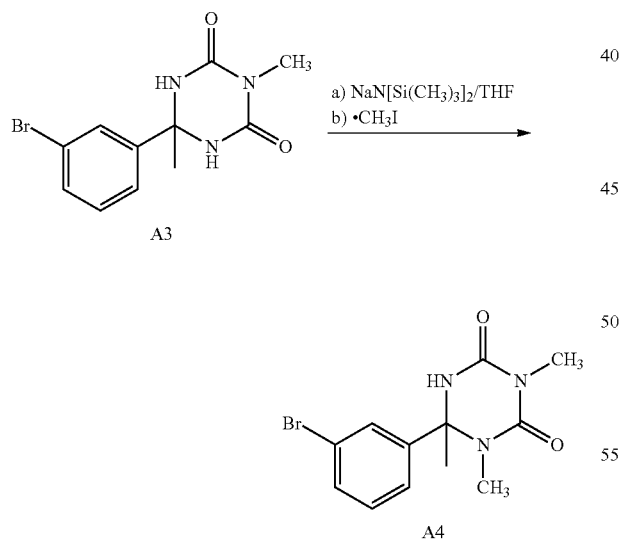

A3 (0.27 g) in THF (50 mL) was treated with 2M sodium (bis(trimethylsilyl) amide (0.38 mL). After 2 h, methyl iodide (0.048 mL) was added and the resultant mixture was stirred at rt for 18 h. The reaction mixture was concentrated in vacuo and partitioned between EtOAc and 1 N HCl. The EtOAc layer was dried over MgSO$_4$ and concentrated. The residue was purified by prep TLC using DCM to give A4.

Step 5:

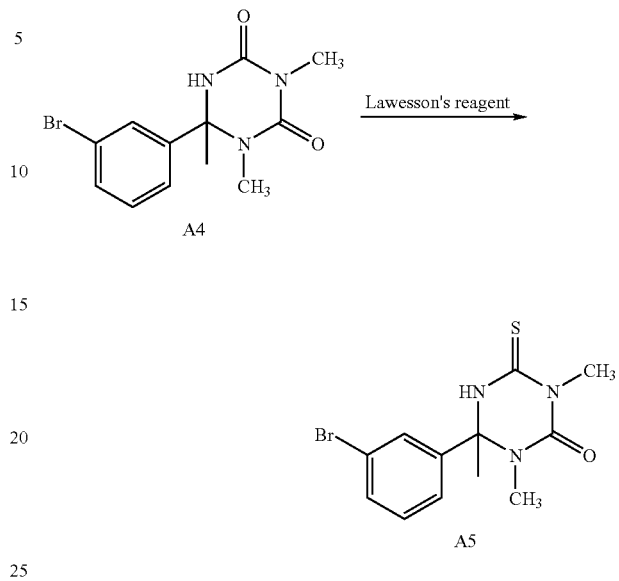

A4 (0.28 g) in toluene (12 mL) was treated with Lawesson's reagent (0.24 g) and heated in a sealed tube at 100° C. for 20 hr, then concentrated and the residue purified by prep TLC using DCM to collect compound A5 (0.18 g).

Step 6:

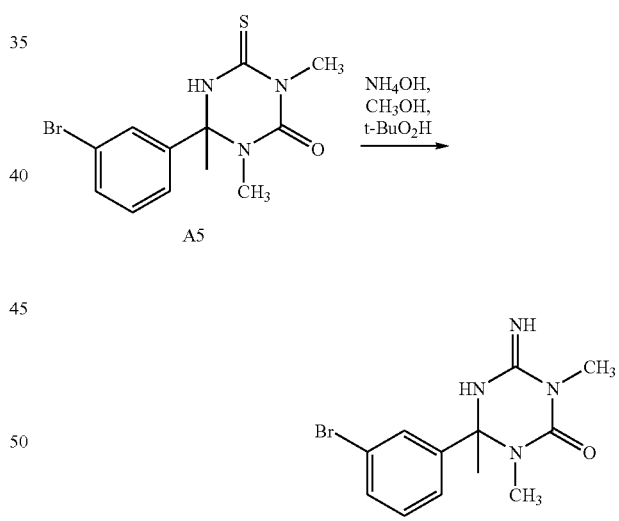

A mixture of A5 (0.18 g) in MeOH (9 mL), NH$_4$OH (7.5 mL) and t-butyl hydroperoxide (2.25 mL) was stirred at rt for 48 hr. The reaction mixture was concentrated in vacuo to give a white residue which was purified by prep TLC to elute Example 1 with DCM/MeOH 19:1 (0.094 g).

NMR (DMSO-d6): 1.80 3H, s, 2.90 3H, s, 3.2 3H, s, 7.23 1H, d, 7.27 1H, d, 7.41 1H dd, 7.49 1H, d.

LCMS: $M^{+H}$ 311, (RT 2.26 min)

Compound Example 2

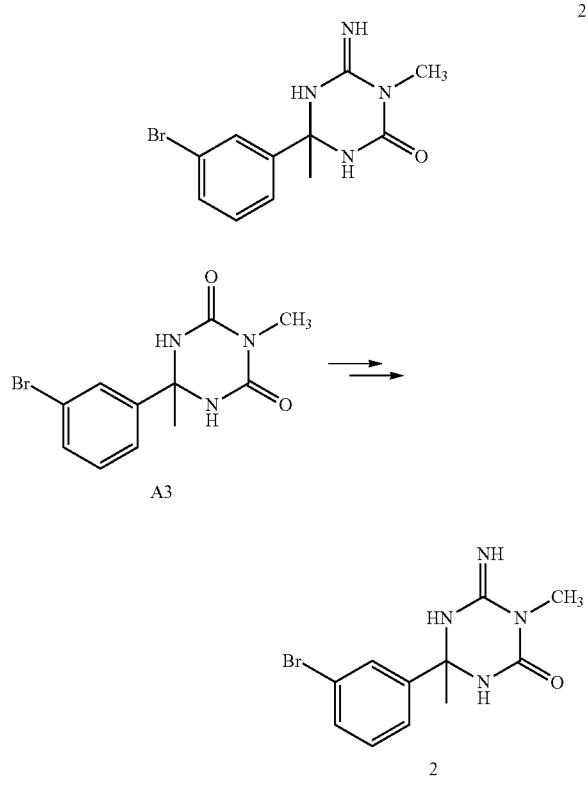

Example 2 was prepared by starting with A3, prepared above in Example 1, and following steps 5 and 6.

NMR (DMSO-d6) 1.47 3H s 2.91 3H s 7.28 1H t 7.42 2H d 7.58 1H s

LCMS: M$^{+H}$ 297/299 (RT 2.12 min)

Compound Example 3

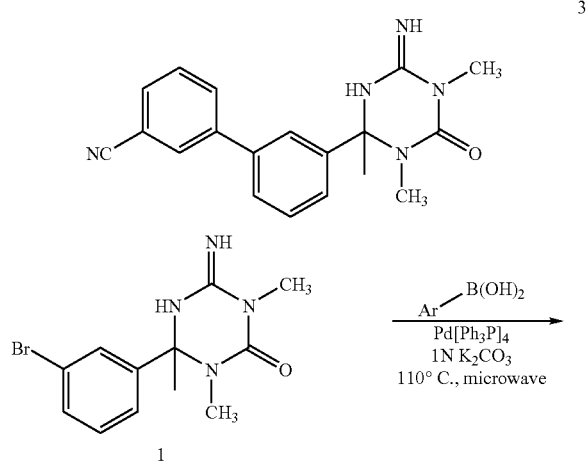

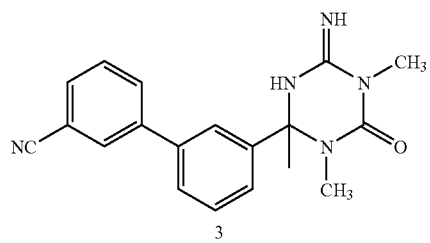

A mixture of Example 1 (0.012 g) and 3-cyanophenylboronic acid (0.015 g) palladium tetrakis-triphenylphosphine (0.015 g) EtOH (2 mL) and 1 N K$_2$CO$_3$ (0.3 mL) was purged with argon and the sealed vial was heated to 110° C. in a microwave reactor for 30 min. After cooling to rt the mixture was filter through a 2 g silica gel-carbonate cartridge using DCM. The DCM solution was then placed on a prep TLC plate to elute Example 3 (0.005 g) using DCM/MeOH 19:1.

NMR (DMSO-d6): 1.74 3H s 2.79 3H s 2.89 3H s 7.30 1H d 7.45 1H t 7.58 1H s 7.61 1H d 7.66 1H t 7.82 1H d 7.95 1H d 8.11 1H s.

LCMS M$^{+H}$ 334 (RT 2.49 min)

Following the procedure for Example 3 and using the appropriate aryl boronic acids gave the following additional Examples 4, 5, 6 and 7.

Compound Example 4

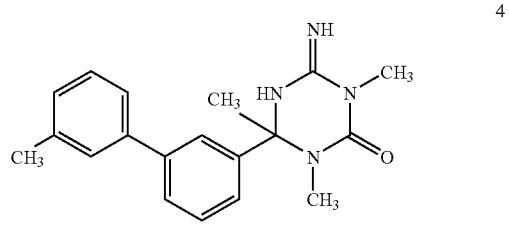

LCMS M$^{+H}$ 323 (RT 2.75 min)

NMR (DMSO-d6): 1.71 3H s 2.35 3H s 2.79 3H s 2.91 3H s 7.16 1H d 7.28 1H d 7.33-7.4 4H m 7.46-7.49 2H m.

Compound Example 5

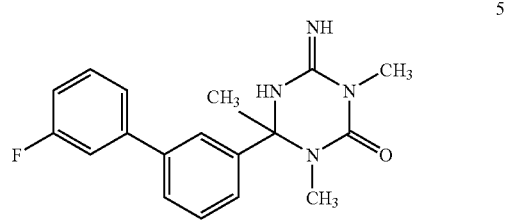

LCMS M+H 327 (RT 2.63 min)
NMR (DMSO-d6): 1.71 3H s 2.79 3H s 2.97 3H s 7.19 1H t 7.26 1H d 7.39-7.55 6H m.

Compound Example 6

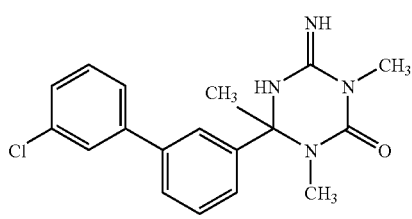

LCMS M+H 343 (RT 2.80 min)
NMR (DMSO-d6): 1.72 3H s 2.80 3H s 2.97 3H s 7.27 1H d 7.42 2H m 7.44 2H m 7.55 2H t 7.64 1H s.

Compound Example 7

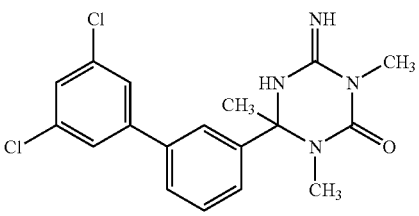

CMS M+H 377 (RT 3.14 min)
NMR (DMSO-d6): 1.72 3H s 2.79 3H s 2.90 3H s 7.28 1H s 7.42 1H t 7.53 1H s 7.58-7.60 2H m 7.66 2H s.

Compound Example 8

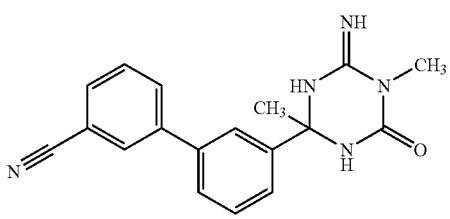

Following the procedure of Example 3 but using Example 2 as the starting material provided Example 8.
LCMS M+H 320 (RT 2.28 min)
NMR (DMSO-d6): 1.50 3H s 2.90 3H s 7.41 1H t 7.47 1H d 7.57 1H d 7.67 1H d 7.78 1H s 7.83 1H d 7.96 1H d 8.08 1H s.

The following assays may be used to determine the biological activity of the compounds of formula I:

Human Cathepsin D FRET Assay

The substrate described below is described in Y. Yasuda et al., *J. Biochem.*, 125, 1137 (1999). Substrate and enzyme are commercially available. A Km of 4 uM is determined for the substrate below under the assay conditions described and is consisitent with Yasuda et al.

The assay is run in a 30 ul final volume using a 384 well Nunc black plate. 8 concentrations of compound are pre-incubated with enzyme for 30 mins at 37C followed by addition of substrate with continued incubation at 37C for 45 mins. The rate of increase in fluorescence is linear for over 1 h and is measured at the end of the incubation period using a Molecular Devices FLEX station plate reader. Kis are interpolated from the IC50s using a Km value of 4 uM and the substrate concentration of 2.5 uM.

Reagents
Na-Acetate pH 5
1% Brij-35 from 10% stock (Calbiochem)
DMSO
Purified (>95%) human liver Cathepsin D (Athens Research & Technology Cat# 16-12-030104)
Peptide substrate(Km=4 uM) Bachem: product M-2455 Mca-Gly-Lys-Pro-lle-Leu-Phe-Arg-Leu-Lys(Dnp)-D-Arg-N H$_2$
Pepstatin is used as a control inhibitor (Ki~0.5 nM) and is available from Sigma.
Nunc 384 well black plates
Final Assay Buffer Conditions
100 mM Na Acetate pH 5.0
0.02% Brij-35
1% DMSO Compound is diluted to 3× final concentration in assay buffer containing 3% DMSO. 10 ul of compound is added to 10 ul of 2.25 nM enzyme(3×) diluted in assay buffer without DMSO, mixed briefly, spun, and incubated at 37C for 30 mins. 3× substrate (7.5 uM) is prepared in 1× assay buffer without DMSO. 10 ul of substrate is added to each well mixed and spun briefly to initiate the reaction. Assay plates are incubated at 37 C for 45 mins and read on 384 compatible fluorescence plate reader using a 328 nm Ex and 393 nm Em.

BACE-1 Cloninq, Protein Expression and Purification

A predicted soluble form of human BACE1 (sBACE1, corresponding to amino acids 1-454) is generated from the full length BACE1 cDNA (full length human BACE1 cDNA in pcDNA4/mycHisA construct; University of Toronto) by PCR using the advantage-GC cDNA PCR kit (Clontech, Palo Alto, Calif.). A HindIII/PmeI fragment from pcDNA4-sBACE1 myc/His is blunt ended using Klenow and subcloned into the Stu I site of pFASTBACI(A) (Invitrogen). A sBACE1mycHis recombinant bacmid is generated by transposition in DH10Bac cells(GIBCO/BRL). Subsequently, the sBACE1 mycHis bacmid construct is transfected into sf9 cells using CellFectin (Invitrogen, San Diego, Calif.) in order to generate recombinant baculovirus. Sf9 cells are grown in SF 900-II medium (Invitrogen) supplemented with 3% heat inactivated FBS and 0.5× penicillin/streptomycin solution (Invitrogen). Five milliliters of high titer plaque purified sBACEmyc/His virus is used to infect 1 L of logarithmically growing sf9 cells for 72 hours. Intact cells are pelleted by centrifugation at 3000×g for 15 minutes. The supernatant, containing secreted sBACE1, is collected and diluted 50% v/v with 100 mM HEPES, pH 8.0. The diluted medium is loaded onto a Q-sepharose column. The Q-sepharose column is washed with Buffer A (20 mM HEPES, pH 8.0, 50 mM NaCl).

Proteins, are eluted from the Q-sepharose column with Buffer B (20 mM HEPES, pH 8.0, 500 mM NaCl). The protein peaks from the Q-sepharose column were pooled and loaded onto a Ni-NTA agarose column. The Ni-NTA column was then washed with Buffer C (20 mM HEPES, pH 8.0, 500 mM NaCl). Bound proteins are then eluted with Buffer D (Buffer C+250 mM imidazole). Peak protein fractions are determined by the Bradford Assay (Biorad, Calif.) are concentrated using a Centricon 30 concentrator (Millipore). sBACE1 purity is estimated to be ~90% as assessed by SDS-PAGE and Commassie Blue staining. N-terminal sequencing indicates that greater than 90% of the purified sBACE1 contained the prodomain; hence this protein is referred to as sproBACE1.

Peptide Hydrolysis Assay

The inhibitor, 25 nM EuK-biotin labeled APPsw substrate (EuK-KTEEISEVNLDAEFRHDKC-biotin; CIS-Bio International, France), 5 µM unlabeled APPsw peptide (KTEEISEVNLDAEFRHDK; American Peptide Company, Sunnyvale, Calif.), 7 nM sproBACE1, 20 mM PIPES pH 5.0, 0.1% Brij-35 (protein grade, Calbiochem, San Diego, Calif.), and 10% glycerol are preincubated for 30 min at 30° C. Reactions are initiated by addition of substrate in a 5 µl aliquot resulting in a total volume of 25 µl. After 3 hr at 30° C. reactions are terminated by addition of an equal volume of 2× stop buffer containing 50 mM Tris-HCl pH 8.0, 0.5 M KF, 0.001% Brij-35, 20 µg/ml SA-XL665 (cross-linked allophycocyanin protein coupled to streptavidin; CIS-Bio International, France) (0.5 µg/well). Plates are shaken briefly and spun at 1200×g for 10 seconds to pellet all liquid to the bottom of the plate before the incubation. HTRF measurements are made on a Packard Discovery® HTRF plate reader using 337 nm laser light to excite the sample followed by a 50 µs delay and simultaneous measurements of both 620 nm and 665 nm emissions for 400 µs.

$IC_{50}$ determinations for inhibitors, (I), are determined by measuring the percent change of the relative fluorescence at 665 nm divided by the relative fluorescence at 620 nm, (665/620 ratio), in the presence of varying concentrations of I and a fixed concentration of enzyme and substrate. Nonlinear regression analysis of this data is performed using GraphPad Prism 3.0 software selecting four parameter logistic equation, that allows for a variable slope. Y=Bottom+(Top-Bottom)/(1+10^((LogEC50−X)*Hill Slope)); X is the logarithm of concentration of I, Y is the percent change in ratio and Y starts at bottoUsing the above assay, the $K_i$ values of the compounds of Examples 1 to 9 and 12 to 20 were determined. The $K_i$ values ranged from 1 to 1,000,000 nM, with some preferred compound exhibiting $K_i$ values of less than 100 nMm and goes to top with a sigmoid shape.

Using the above assay, the $K_i$ values of the compounds of Examples 1 to 8 were determined. The $K_i$ values were in the range of about 1300 nM to about 48,000 nM, with Example 7 having a $K_i$ value 1363 nM.

Human Mature Renin Enzyme Assay:

Human Renin is cloned from a human kidney cDNA library and C-terminally epitope-tagged with the V5-6His sequence into pCDNA3.1. pCNDA3.1-Renin-V5-6His is stably expressed in HEK293 cells and purified to >80% using standard Ni-Affinity chromatography. The prodomain of the recombinant human renin-V5-6His is removed by limited proteolysis using immobilized TPCK-trypsin to give mature-human renin. Renin enzymatic activity is monitored using a commercially available fluorescence resonance energy transfer(FRET) peptide substrate, RS-1 (Molecular Probes, Eugene, Oreg.) in 50 mM Tris-HCl pH 8.0, 100 mM NaCl, 0.1% Brij-35 and 5% DMSO buffer for 40 mins at 30 degrees celsius in the presence or absence of different concentrations of test compounds. Mature human Renin is present at approximately 200 nM. Inhibitory activity is defined as the percent decrease in renin induced fluorescence at the end of the 40 min incubation compared to vehicle controls and samples lacking enzyme.

In the aspect of the invention relating to a combination of a compound of formula I with a cholinesterase inhibitor, acetyl- and/or butyrylchlolinesterase inhibitors can be used. Examples of cholinesterase inhibitors are tacrine, donepezil, rivastigmine, galantamine, pyridostigmine and neostigmine, with tacrine, donepezil, rivastigmine and galantamine being preferred.

In the aspect of the invention relating to a combination of a compound of formula I with at least one additional pharmaceutical agent. Non-limiting examples of additional pharmaceutical agents include, for example, muscarinic antagonist, $m_1$ or $m_2$ antagonists can be used. Examples of $m_1$ antagonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

Other example of pharmaceutical agents include beta secretase inhibitors; HMG-CoA reductase inhibitors, such as atorvastatin, lovastatin, simvistatin, pravastatin, fluvastatin and rosuvastatin; non-steroidal anti-inflammatory agents, such as ibuprofen, N-methyl-D-aspartate receptor antagonists, such as memantine, anti-amyloid antibodies including humanized monoclonal antibodies; vitamin E; nicotinic acetylcholine receptor agonists; CB1 receptor inverse agonists or CB1 receptor antagonists; antibiotics, e.g., docycycline; growth hormone secretagogues; histamine H3 antagonists; AMPA agonists; PDE4 inhibitors; $GABA_A$ inverse agonists; inhibitors of amyloid aggregartion; glycogen synthase kinase beta inhibitors; promoters of alpha secretase activity, and cholesterol absorption inhibitors, e.g. bile sequestants azetidiones, such as ezetimibe (ZETIA).

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution—refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

When a compound of formula I is used in combination with a cholinesterase inhibitor to treat cognitive disorders, these two active components may be co-administered simultaneously or sequentially, or a single pharmaceutical composition comprising a compound of formula I and a cholinesterase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the cholinesterase inhibitor can be determined from published material, and may range from 0.001 to 100 mg/kg body weight.

When separate pharmaceutical compositions of a compound of formula I and a cholinesterase inhibitor are to be administered, they can be provided in a kit comprising in a single package, one container comprising a compound of formula I in a pharmaceutically acceptable carrier, and a separate container comprising a cholinesterase inhibitor in a pharmaceutically acceptable carrier, with the compound of formula I and the cholinesterase inhibitor being present in amounts such that the combination is therapeutically effective. A kit is advantageous for administering a combination when, for example, the components must be administered at different time intervals or when they are in different dosage forms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound having the structural Formula IA:

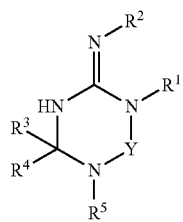

or a stereoisomer, tautomer, or pharmaceutically acceptable salt of said compound, said stereoisomer, or said tautomer, wherein Y is —C(=O)— or —C($R^{6'}R^{7'}$)—;

$R^1$ is selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, —$OR^{15}$, —C(O)$R^8$, —C(O)$OR^9$, —S(O)$R^{10}$, —S(O)$_2R^{10}$, —C(O)N($R^{11}$)($R^{12}$), —S(O)N($R^{11}$)($R^{12}$), —S(O)$_2$N($R^{11}$)($R^{12}$), —$NO_2$, —N=C($R^8$)$_2$ and —N($R^8$)$_2$;

$R^2$ is H;

$R^5$ is selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, aryl-cycloalkenyl, heteroarylcycloalkenyl, heterocycloalkenyl, arylheterocycloalkenyl, heteroaryiheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, —$OR^{15}$, —CN, —C(O)$R^8$, —C(O)$OR^9$, —S(O)$R^{10}$, —S(O)$_2R^{10}$, —C(O)N($R^{11}$)($R^{12}$), —S(O)N($R^{11}$)($R^{12}$), —S(O)$_2$N($R^{11}$)($R^{12}$), —$NO_2$, —N=C($R^8$)$_2$ and —N($R^8$)$_2$;

$R^3$ and $R^4$ are each independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, cycloalkenylheteroaryl, —$CH_2$—O—Si($R^9$)($R^{10}$)($R^{19}$), —CN, —C(O)$R^8$, —C(O)$OR^9$, —C(O)N($R^{11}$)($R^{12}$), —$SR^{19}$, —S(O)N($R^{11}$)($R^{12}$), —S(O)$_2$N($R^{11}$)($R^{12}$), —N($R^{11}$)($R^{12}$), —N($R^{11}$)C(O)$R^8$, —N($R^{11}$)S(O)$R^{10}$, —N($R^{11}$)S(O)$_2R^{10}$—, —N($R^{11}$)C(O)N($R^{12}$)($R^{13}$), —N($R^{11}$)C(O)$OR^9$ and —C(=NOH)$R^8$;

$R^{6'}$ and $R^{7'}$, together with the carbon atom to which they are attached, form a 3- to 7-membered cycloalkyl ring optionally substituted by 1 to 5 $R^{14}$ moieties or oxo;

or, optionally, $R^{6'}$ and $R^7$, together with the carbon atom to which they are attached, form a 3- to 7-membered cycloalkylether group having one oxygen atom optionally substituted by 1 to 5 $R^{14}$ moieties or oxo;

or optionally, $R^3$ and $R^4$, together with the carbon atom to which they are attached, form a 3—to 7—membered cycloalkyl ring optionally substituted by 1 to 5 $R^{14}$ moieties and/or oxo;

or, optionally, $R^3$ and $R^4$, together with the carbon atom to which they are attached, form a 3- to 7-membered cycloalkylether group having one oxygen atom optionally substituted by 1 to 5 $R^{14}$ moieties and/or oxo;

or, optionally, $R^4$ and $R^5$, together with the atoms to which they are shown attached, form a 4- to 7-membered heterocyclyl, heterocyclenyl or heteroaryl ring having, in addition to the N atom, 1 or 2 additional hetero atoms selected from the group consisting of O, N, —N(R)— and S, wherein said rings are optionally substituted by 1 to 5 independently selected $R^{14}$ moieties and/or by oxo when said rings are heterocyclyl or heterocyclenyl;

or, optionally, when $R^4$ and $R^5$ together form a 4- to 7-membered heterocyclyl, heterocyclenyl or heteroaryl ring and X is N($R^1$) and Y is —C($R^{6'}$)($R^7$)—, then $R^1$ and $R^{6'}$ together form a 3- to 7-membered cycloalkyl, cycloalkenyl, heterocyclyl, heterocyclenyl, aryl or heteroaryl ring having 0 to 3 heteroatoms selected from the group consisting of O, N, —N(R)— and S, wherein said rings are optionally substituted by 1 to 5 independently selected $R^{14}$ moieties and/or by oxo when said rings are cycloalkyl, cycloalkenyl, heterocyclyl or heterocyclenyl, provided that i) $R^4$ and $R^5$ and ii) $R^5$ and $R^{6'}$ do not simultaneously cyclize to form a ring;

or, optionally, $R^3$ and $R^4$, together, with the carbon atom to which they are shown attached, or, optionally, $R^{6'}$ and $R^{7'}$, together with the carbon atom to which they are attached, from one of the following multicyclic groups:

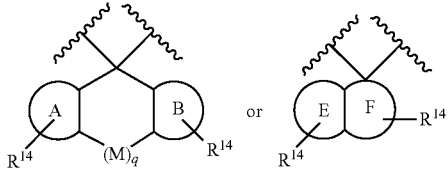

wherein:
  M is independently —(CH$_2$)—, —S—, —N(R$^{19}$)—, —O—, —S(O)—, —S(O)$_2$—, or —C(O)—;
  q is 0, 1, or 2;
  A and B are independently aryl, heteroaryl, cycloalkyl, cycloalkenyl or heterocyclyl;
  E is aryl or heteroaryl; and
  F is cycloalkyl, cycloalkenyl, heterocyclyl or heterocyclenyl
  provided that $R^3$ and $R^4$ and $R^{6'}$ and $R^{7'}$ are not simultaneously combined to form said multicyclic croups:

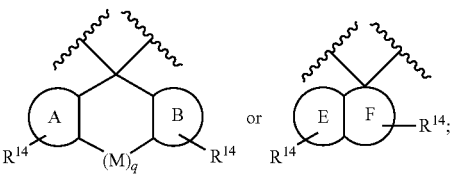

each R is independently hydrogen, alkyl, alkenyl, alkynyl, cycloalkyl, cycloalkenyl, aryl, arylalkyl, heterocycloalkyl, heterocycloalkylalkyl, heteroaryl, heteroarylalkyl, arylcycloalkyl, —OR$^{15}$, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), or —S(O)$_2$N(R$^{11}$)(R$^{12}$);

$R^8$ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, —OR$^{15}$, —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

$R^9$ is independently selected from the group consisting of H, alkyl, alkenyl, alkynyl, cycloalkyl, cycloalkylalkyl, heterocycloalkyl, heterocycloalkylalkyl, aryl, arylalkyl, heteroaryl and heteroarylalkyl;

$R^{10}$ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl and —N(R$^{15}$)(R$^{16}$);

$R^{11}$, $R^{12}$ and $R^{13}$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, —C(O)R$^8$, —C(O)OR$^9$, —S(O)R$^{10}$, —S(O)$_2$R$^{10}$, —C(O)N(R$^{15}$)(R$^{16}$), —S(O)N(R$^{15}$)(R$^{16}$), and —S(O)$_2$N(R$^{15}$)(R$^{16}$);

$R^{14}$ is 1-5 substituents independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

$R^{15}$, $R^{16}$ and $R^{17}$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, arylheterocycloalkyl, R$^{18}$-alkyl, R$^{18}$-cycloalkyl, R$^{18}$-cycloalkylalkyl, R$^{18}$-heterocycloalkyl, R$^{18}$-heterocycloalkylalkyl, R$^{18}$-aryl, R$^{18}$-arylalkyl, R$^{18}$-heteroaryl and R$^{18}$-heteroarylalkyl; or $R^{15}$, $R^{16}$ and $R^{17}$ are

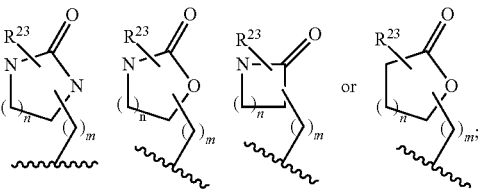

wherein $R^{23}$ numbers 0 to 5 substituents, m is 0 to 6 and n is 1 to 5;

$R^{18}$ is 1-5 substituents independently selected from the group consisting of alkyl, alkenyl, alkynyl, aryl, arylalkyl, arylalkenyl, arylalkynyl, —NO$_2$, halo, heteroaryl, HO-alkyoxyalkyl, —CF$_3$, —CN, alkyl-CN, —C(O)R$^{19}$, —C(O)OH, —C(O)OR$^{19}$, —C(O)NHR$^{20}$, —C(O)NH$_2$, —C(O)NH$_2$—C(O)N(alkyl)$_2$, —C(O)N(alkyl)(aryl), —C(O)N(alkyl)(heteroaryl), —SR$^{19}$, —S(O)$_2$R$^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocycloalkyl), —S(O)$_2$N(alkyl)$_2$, —S(O)$_2$N(alkyl)(aryl), —OCF$_3$, —OH, —OR$^{20}$, —O—heterocycloalkyl, —O—cycloalkylalkyl, —O—heterocycloalkylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$ N(alkyl)(alkyl);

or two $R^{18}$ moieties on adjacent carbons can be linked together to form

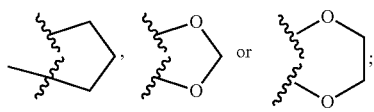

$R^{19}$ is alkyl, cycloalkyl, aryl, arylalkyl or heteroarylalkyl;
$R^{20}$ is alkyl, cycloalkyl, aryl, halo substituted aryl, arylalkyl, heteroaryl or heteroarylalkyl;
and wherein:
  i) each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, Arylalkynyl, Aryl, cycloalkylaryl, heterocycloalkylaryl, cycloalkenylaryl, heterocycloalkenylaryl, heteroaryl, cycloalkylheteroaryl, heterocycloalkylheteroaryl, heterocycloalkenylaryl, in $R^1$, $R^2$, $R^3$, $R^4$, $R^5$, and $R^6$, and ii) each of the alkyl, alkenyl, alkynyl, cycloalkyl, cycloalkylalkyl, cycloalkenyl, arylcycloalkyl, heterocycloalkyl, heterocycloalkylalkyl, aryl, arylalkyl, heteroaryl, heteroarylalkyl, alkenyl and alkynyl groups in R, $R^8$, $R^9$, $R^{10}$, $R^{11}$, $R^{12}$, $R^{13}$ and $R^{14}$, are independently unsubstituted or substituted by 1 to 5 $R^{21}$ groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylaryl, heterocycloalkenylaryl, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, —N$_3$, —NO$_2$ and —S(O)$_2$R$^{15}$; and wherein each of the alkyl, cycloalkenyl, cycloalkyl, cycloalkylalkyl, heterocycloalkyl, heterocycloalkylalkyl, aryl, arylalkyl, heteroaryl, heteroarylalkyl, alkenyl and alkynyl groups in $R^{21}$ are independently unsubstituted or substituted by 1 to 5 $R^{22}$ groups independently selected from the group consisting of alkyl, alkenyl, alkynyl, cycloalkyl, cycloalkenyl, heterocycloalkyl, aryl, heteroaryl, halo, —CF$_3$, —CN, —OR$^{15}$, —C(O)R$^{15}$, —C(O)OR$^{15}$, -alkyl-C(O)OR$^{15}$, C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —N$_3$, —NO$_2$, —S(O)R$^{15}$ and —S(O)$_2$R$^{15}$;

or two $R^{21}$ or two $R^{22}$ moieties on adjacent carbons can be linked together to form

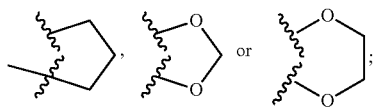

and when $R^{21}$ or $R^{22}$ are selected from the group consisting of —C(=NOR$^{15}$)R$^{16}$, —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$ and —CH$_2$—N(R$^{15}$)C(O)OR$^{16}$, $R^{15}$ and $R^{16}$ together can be a $C_2$ to $C_4$ chain wherein, optionally, one, two or three ring carbons can be replaced by —C(O)— or —N(H)— and $R^{15}$ and $R^{16}$, together with the atoms to which they are attached, form a 5 to 7 membered ring, optionally substituted by $R^{23}$;

$R^{23}$ is 1 to 5 groups independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —OR$^{24}$, —C(O)R$^{24}$, —C(O)OR$^{24}$, —C(O)N(R$^{24}$)(R$^{25}$), —SR$^{24}$, —S(O)N(R$^{24}$)(R$^{25}$), —S(O)$_2$N(R$^{24}$)(R$^{25}$), —C(=NOR$^{24}$)R$^{25}$, —P(O)(OR$^{24}$)(OR$^{25}$), —N(R$^{24}$)(R$^{25}$), -alkyl-N(R$^{24}$)(R$^{25}$), —N(R$^{24}$)C(O)R$^{25}$, —CH$_2$—N(R$^{24}$)C(O)R$^{25}$, —N(R$^{24}$)S(O)R$^{25}$, —N(R$^{24}$)S(O)$_2$R$^{25}$, —CH$_2$—N(R$^{24}$)S(O)$_2$R$^{25}$, —N(R$^{24}$)S(O)$_2$N(R$^{25}$)(R$^{26}$), —N(R$^{24}$)S(O)N(R$^{25}$)(R$^{26}$), —N(R$^{24}$)C(O)N(R$^{25}$)(R$^{26}$), —CH$_2$—N(R$^{24}$)C(O)N(R$^{25}$)(R$^{26}$), —N(R$^{24}$)C(O)OR$^{25}$, —CH$_2$—N(R$^{24}$)C(O)OR$^{25}$, —S(O)R$^{24}$ and —S(O)$_2$R$^{24}$; and wherein each of the alkyl, cycloalkyl, cycloalkylalkyl, heterocycloalkyl, heterocycloalkylalkyl, aryl, arylalkyl, heteroaryl, heteroarylalkyl, alkenyl and alkynyl groups in $R^{23}$ are independently unsubstituted or substituted by 1 to 5 $R^{27}$ groups independently selected from the group consisting of alkyl, cycloalkyl, heterocycloalkyl, aryl, heteroaryl, halo, —CF$_3$, —CN, —OR$^{24}$, —C(O)R$^{24}$, —C(O)OR$^{24}$, alkyl-C(O)OR$^{24}$, C(O)N(R$^{24}$)(R$^{25}$), —SR$^{24}$, —S(O)N(R$^{24}$)(R$^{25}$), —S(O)$_2$N(R$^{24}$)(R$^{25}$), —C(=NOR$^{24}$)R$^{25}$, —P(O)(OR$^{24}$)(OR$^{25}$), —N(R$^{24}$)(R$^{25}$), -alkyl-N(R$^{24}$)(R$^{25}$), —N(R$^{24}$)C(O)R$^{25}$, —CH$_2$—N(R$^{24}$)C(O)R$^{25}$, —N(R$^{24}$)S(O)R$^{25}$, —N(R$^{24}$)S(O)$_2$R$^{25}$, —CH$_2$—N(R$^{24}$)S(O)$_2$R$^{25}$, —N(R$^{24}$)S(O)$_2$N(R$^{25}$)(R$^{26}$), —N(R$^{24}$)S(O)N(R$^{25}$)(R$^{26}$), —N(R$^{24}$)C(O)N(R$^{25}$)(R$^{26}$), —CH$_2$—N(R$^{24}$)C(O)N(R$^{25}$)(R$^{26}$), —N(R$^{24}$)C(O)OR$^{25}$, —CH$_2$—N(R$^{24}$)C(O)OR$^{25}$, —S(O)R$^{24}$ and —S(O)$_2$R$^{24}$;

$R^{24}$, $R^{25}$ and $R^{26}$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, $R^{27}$-alkyl, $R^{27}$-cycloalkyl, $R^{27}$-cycloalkylalkyl, $R^{27}$-heterocycloalkyl, $R^{27}$-heterocycloalkylalkyl, $R^{27}$-aryl, $R^{27}$-arylalkyl, $R^{27}$-heteroaryl and $R^{27}$-heteroarylalkyl;

$R^{27}$ is 1-5 substituents independently selected from the group consisting of alkyl, alkenyl, alkynyl, aryl, arylalkyl, —NO$_2$, halo, —CF$_3$, —CN, alkyl-CN, —C(O)R$^{28}$, —C(O)OH, —C(O)OR$^{28}$, —C(O)NHR$^{29}$, —C(O)N(alkyl)$_2$, —C(O)N(alkyl)(aryl), —C(O)N(alkyl)(heteroaryl), —SR$^{28}$, —S(O)$_2$R$^{29}$, —S(O)NH$_2$, —S(O)NH(alkyl), —S(O)N(alkyl)(alkyl), —S(O)NH(aryl), —S(O)$_2$NH$_2$, —S(O)$_2$NHR$^{28}$, —S(O)$_2$NH(aryl), —S(O)$_2$NH(heterocycloalkyl), —S(O)$_2$N(alkyl)$_2$, —S(O)$_2$N(alkyl)(aryl), —OH, —OR$^{29}$, —O-heterocycloalkyl, —O-cycloalkylalkyl, —O-heterocycloalkylalkyl, —NH$_2$, —NHR$^{29}$, —N(alkyl)$_2$, —N(arylalkyl)$_2$, —N(arylalkyl)(heteroarylalkyl), —NHC(O)R$^{29}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{29}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

R$^{28}$ is alkyl, alkenyl, alkynyl, cycloalkyl, arylalkyl or heteroarylalkyl; and R$^{29}$ is alkyl, alkenyl, alkynyl, cycloalkyl, aryl, arylalkyl, heteroaryl or heteroarylalkyl.

2. A compound of claim 1, or a tautomer or stereoisomer thereof, or a pharmaceutically acceptable salt of said compound, said tautomer, or said stereoisomer, said compound having the structure:

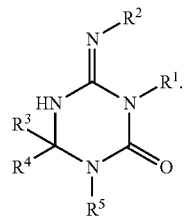

IA

3. A compound of claim 2, or a tautomer or stereoisomer thereof, or a pharmaceutically acceptable salt of said compound, said tautomer, or said stereoisomer, wherein:

R$^1$ is alkyl, R$^{21}$-alkyl or cycloalkyl;

R$^2$ is H;

R$^3$ is R$^{21}$-aryl or R$^{21}$-heteroaryl

R$^4$ is alkyl and

R$^5$ is hydrogen, alkyl, cycloalkyl, aryl, heteroaryl, or heteroarylalkyl.

4. A compound according to claim 1, or a tautomer or stereoisomer thereof, or a pharmaceutically acceptable salt of said compound, said tautomer, or said stereoisomer, said compound having the structure IE:

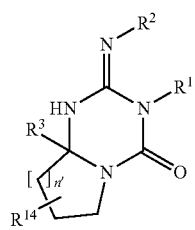

IE where n' is an integer from 0 to 3.

5. A compound of claim 1, or a tautomer or stereoisomer thereof, or a pharmaceutically acceptable salt of said compound, said tautomer, or said stereoisomer, wherein said compound is selected from the group consisting of:

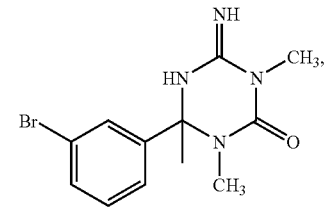

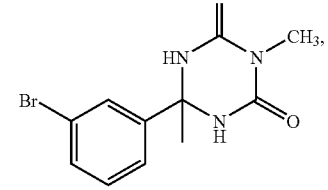

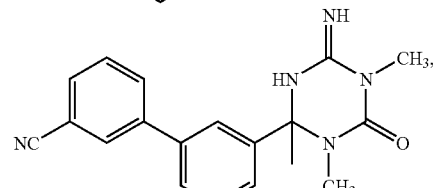

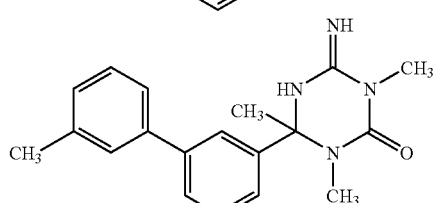

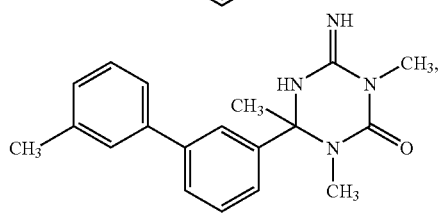

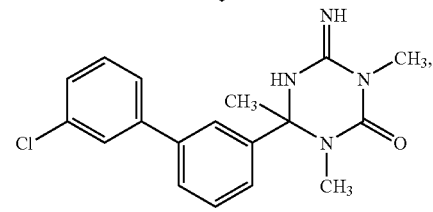

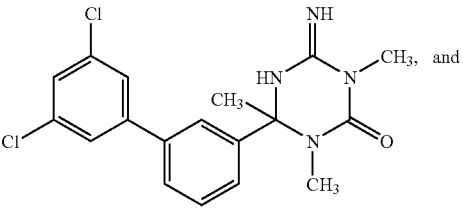

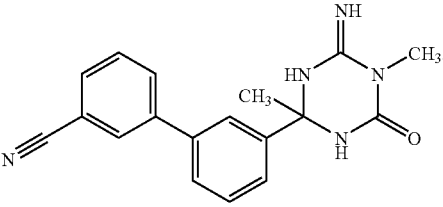

6. A pharmaceutical composition comprising an effective amount of a compound of claim 1, or a tautomer or stereoisomer thereof, or a pharmaceutically acceptable salt of said compound, said tautomer, or said stereoisomer, and a pharmaceutically effective carrier.

7. A pharmaceutical composition comprising an effective amount of a compound of claim 1, or a tautomer or stereoisomer thereof, or a pharmaceutically acceptable salt of said compound, said tautomer, or said stereoisomer, and an effective amount of a cholinesterase inhibitor, a muscarinic $m_2$ antagonist or a muscarinic $m_1$ agonist in a pharmaceutically effective carrier.

8. A pharmaceutical composition comprising an effective amount of a compound of claim 1, or a tautomer or stereoisomer thereof, or a pharmaceutically acceptable salt of said compound, said tautomer, or said stereoisomer, and at least one second pharmaceutical agent selected from the group consisting of beta secretase inhibitors; gamma secretase inhibitors; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregartion; glycogen synthase kinase beta inhibitors; promoters of alpha secretase activity or a cholesterol absorption inhibitor.

9. A compound of claim 1, or a tautomer or stereoisomer thereof, or a pharmaceutically acceptable salt of said compound, said tautomer, or said stereoisomer, wherein:
  $R^3$ and $R^4$ are each independently selected from the group consisting of alkyl, cycloalkyl, cycloalkylalkyl, heterocycloalkylalkyl, aryl, arylalkyl, heteroaryl, heteroarylalkyl, —$CH_2$—O—$Si(R^9)(R^{10})(R^{19})$, —CN, —C(O)$R^8$, —C(O)O$R^5$, —C(O)N($R^{11}$)($R^{12}$), —$SR^{19}$, —S(O)N($R^{11}$)($R^{12}$), —S(O)$_2$N($R^{11}$)($R^{12}$), —N($R^{11}$)($R^{12}$), —N($R^{11}$)C(O)$R^8$, —N($R^{11}$)S(O)$R^{10}$, —N($R^{11}$)C(O)N($R^{12}$)($R^{13}$), —N($R^{11}$)C(O)O$R^9$ and —C(=NOH)$R^8$.

10. A compound of claim 2, or a tautomer or stereoisomer thereof, or a pharmaceutically acceptable salt of said compound, said tautomer, or said stereoisomer, wherein:
  $R^3$ and $R^4$ are each independently selected from the group consisting of aryl, heteroaryl, heteroarylalkyl, arylalkyl, cycloalkyl, heterocycloalkylalkyl, alkyl and cycloalkylalkyl;

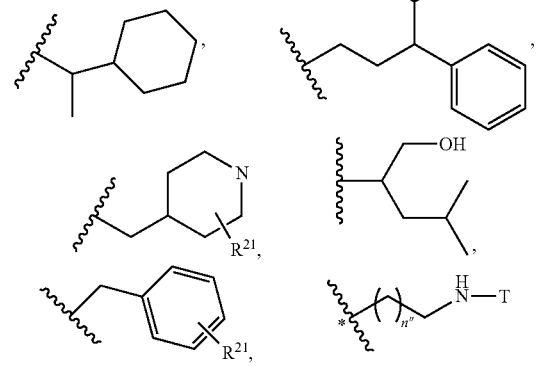

where T is R"C(O)—, R"S(O)$_2$, R"NCO— and n" is 1 to 4,

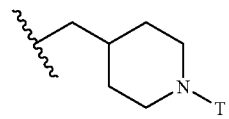

where T is R"C(O)—, R"S(O)$_2$, R"NCO— and n" is 1 to 4,
where R" is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl;

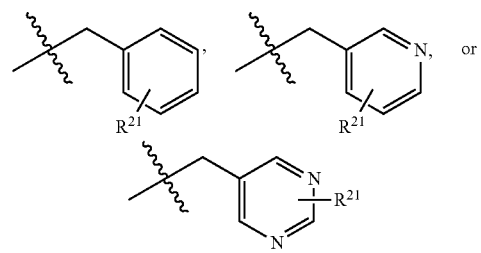

and
  $R^3$ and $R^4$ are each independently methyl, ethyl, cyclopropyl,

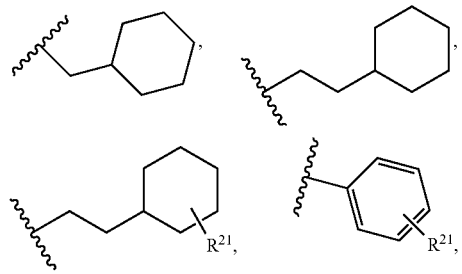

11. A compound of claim 2, or a tautomer or stereoisomer thereof, or a pharmaceutically acceptable salt of said compound, said tautomer, or said stereoisomer, wherein:
  $R^1$ is H, alkyl, $R^{21}$-alkyl, cycloalkyl, arylalkyl, $R^{21}$-arylalkyl, cycloalkylalkyl, $R^{21}$-cycloalkylalkyl, heterocycloalkyalkyl or $R^{21}$-heterocycloalkylalkyl,
  $R^2$ is H;
  $R^3$ is alkyl, cycloalkylalkyl, cycloalkyl, aryl, arylalkyl, $R^{21}$-alkyl, $R^{21}$-cycloalkylalkyl, $R^{21}$-cycloalkyl, $R^{21}$-aryl, $R^{21}$-arylalkyl, or $R^{21}$-heteroaryl;
  $R^4$ is alkyl, cycloalkylalkyl, cycloalkyl, aryl, arylalkyl, $R^{21}$-alkyl, $R^{21}$-cycloalkylalkyl, $R^{21}$-cycloalkyl, $R^{21}$-aryl, $R^{21}$-arylalkyl, or $R^{21}$-heteroaryl;
  $R^5$ is H, alkyl, $R^{21}$-alkyl, cycloalkyl, aryl, arylalkyl, $R^{21}$-arylalkyl, cycloalkylalkyl, $R^{21}$-cycloalkylalkyl, heteroaryl, heteroarylalkyl, heterocycloalkyalkyl or $R^{21}$-heterocycloalkylalkyl;

$R^{15}$, $R^{16}$ and $R^{17}$ is H, $R^{18}$-alkyl, alkyl or

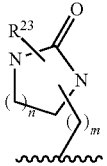

$R^{21}$ is alkyl, aryl, halo, —$OR^{15}$, —$NO_2$, —$C(O)R^{15}$, —$CH_2$—$N(R^{15})C(O)N(R^{16})(R^{17})$ or —$CH(R^{15})(R^{16})$;
n is 1;
m is 1;
$R^{18}$ is —$OR^{20}$
$R^{20}$ is aryl; and
$R^{23}$ is alkyl.

12. A compound of claim 1, or a tautomer or stereoisomer thereof, or a pharmaceutically acceptable salt of said compound, said tautomer, or said stereoisomer, wherein:
$R^1$ is H, $CH_3$, —$CH_2CF_3$, cyclopropyl,

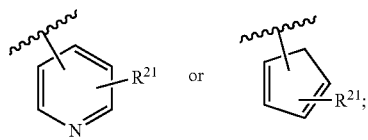

wherein each $R^{21}$ is independently alkyl, halo, phenyl, $R^{22}$-phenyl, wherein each $R^{22}$ is indendently alkyl, halo or —$OR^{15}$.

13. A compound of claim 2, or a tautomer or stereoisomer thereof, or a pharmaceutically acceptable salt of said compound, said tautomer, or said stereoisomer, wherein:
$R^1$ is —$CH_3$;
$R^5$ is H, $CH_3$, or cyclopropyl;
$R^2$ is H;
$R^3$ is alkyl, cycloalkylalkyl, cycloalkyl, aryl, arylalkyl, $R^{21}$-alkyl, $R^{21}$-cycloalkylalkyl, $R^{21}$-cycloalkyl, $R^2$-aryl, $R^{21}$-arylalkyl, heteroarylalkyl, heteroaryl, heterocycloalkylalkyl, $R^{21}$-heteroarylalkyl, $R^{21}$-heteroaryl, $R^{21}$-heterocycloalkyl or $R^{21}$-heterocycloalkylalkyl;
$R^4$ is alkyl, cycloalkylalkyl, cycloalkyl, aryl, arylalkyl, $R^{21}$-alkyl, $R^{21}$-cycloalkylalkyl, $R^{21}$-cycloalkyl, $R^{21}$-aryl, $R^{21}$-arylalkyl, heteroarylalkyl, heteroaryl, heterocycloalkylalkyl, $R^{21}$-heteroarylalkyl, $R^{21}$-heteroaryl, $R^{21}$-heterocycloalkyl or $R^{21}$-heterocycloalkylalkyl;
$R^5$ is H, alkyl, $R^{21}$-alkyl, arylalkyl, $R^{21}$-arylalkyl, cycloalkylalkyl, $R^{21}$-cycloalkylalkyl, heterocycloalkylalkyl or $R^{21}$-heterocycloalkylalkyl;
$R^{15}$, $R^{16}$ and $R^{17}$ is H, cycloalkyl, cycloalkylalkyl, $R^{18}$-alkyl, alkyl, aryl, $R^{18}$-aryl, $R^{18}$-arylalkyl, arylalkyl,

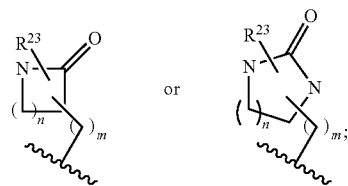

n is 1 or 2;
m is 0 or 1;
$R^{18}$ is —$OR^{20}$ or halo;
$R^{20}$ is aryl or halo substituted aryl;
$R^{21}$ is alkyl, aryl, heteroaryl, $R^{22}$-alkyl, $R^{22}$-aryl, $R^{22}$-heteroaryl, halo, heterocycloalkyl, —$N(R^{15})(R^{16})$, —$OR^{15}$, —$NO_2$, —$C(O)R^{15}$, —$N(R^{15})C(O)R^{16}$, —$N(R^{15})S(O)_2R^{16}$, —$CH_2$—$N(R^{15})C(O)N(R^{16})(R^{17})$, —$N(R^{15})C(O)N(R^{16})(R^{17})$ or —$CH(R^{15})(R^{16})$;
$R^{22}$ is —$OR^{15}$, halo, alkenyl, —$C\equiv C(CH_3)$, or —CN and
$R^{23}$ is H or alkyl.

14. A compound of claim 2, or a tautomer or stereoisomer thereof, or a pharmaceutically acceptable salt of said compound, said tautomer, or said stereoisomer, wherein:
$R^1$ is hydrogen, alkyl, $R^{21}$-alkyl, cycloalkyl, $R^{21}$-cycloalkyl, arylalkyl, $R^{21}$-arylalkyl, heterocyclalkylalkyl, $R^{21}$-heterocyclalkyl, or $R^{21}$-arylalkyl;
$R^2$ is H;
$R^3$ is $R^{21}$-aryl;
$R^4$ is alkyl, $R^{21}$-alkyl, cycloalkyl, $R^{21}$-cycloalkyl, aryl or $R^{21}$-aryl; and
$R^5$ is H, alkyl, cycloalkyl, aryl, heteroaryl, arylalkyl or heteroarylalkyl.

15. A compound having the structural formula IA:

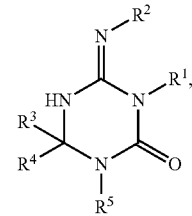

IA wherein:
$R^1$ is $C_1$-$C_6$ alkyl;
$R^2$ is H;
$R^3$ is phenyl optionally substituted with $R^{21}$;
$R^{21}$ is halogen or phenyl optionally substituted with $R^{22}$;
$R^{22}$ is methyl, cyano, or halo;
$R^4$ is $C_1$-$C_6$ alkyl; and
$R^5$ is hydrogen, $C_1$-$C_6$ alkyl.

\* \* \* \* \*